United States Patent
Forgione et al.

(10) Patent No.: US 10,675,102 B2
(45) Date of Patent: Jun. 9, 2020

(54) ROBOT, PARTICULARLY FOR MINI-INVASIVE SURGERY THROUGH A SINGLE PARIETAL INCISION OR NATURAL ORIFICE

(71) Applicant: VALUEBIOTECH S.R.L., Milan (IT)

(72) Inventors: Antonello Forgione, Milan (IT); Louis Judah Jauvtis, Safnern (CH); Renzo Zaltieri, Agrate Brianza (IT)

(73) Assignee: VALUEBIOTECH S.R.L., Milan (IT)

( * ) Notice: Subject to any disclaimer, the term of this patent is extended or adjusted under 35 U.S.C. 154(b) by 416 days.

(21) Appl. No.: 14/786,784

(22) PCT Filed: Apr. 23, 2014

(86) PCT No.: PCT/EP2014/058199
§ 371 (c)(1),
(2) Date: Oct. 23, 2015

(87) PCT Pub. No.: WO2014/173932
PCT Pub. Date: Oct. 30, 2014

(65) Prior Publication Data
US 2016/0066999 A1    Mar. 10, 2016

(30) Foreign Application Priority Data

Apr. 23, 2013    (IT) .............................. MI2013A0666

(51) Int. Cl.
*A61B 34/00* (2016.01)
*A61B 34/30* (2016.01)
(Continued)

(52) U.S. Cl.
CPC ............ *A61B 34/30* (2016.02); *A61B 1/0016* (2013.01); *A61B 1/00147* (2013.01);
(Continued)

(58) Field of Classification Search
CPC ......... A61B 34/30; A61B 34/99; A61B 34/20; A61B 2034/302; A61B 2034/303;
(Continued)

(56) References Cited

U.S. PATENT DOCUMENTS

2002/0143319 A1    10/2002    Brock
2009/0054909 A1 *   2/2009    Farritor .............. A61B 19/2203
                                                    606/130

(Continued)

FOREIGN PATENT DOCUMENTS

WO        2013026012 A1    2/2013

OTHER PUBLICATIONS

International Search Report and Written Opinion dated May 22, 2014 re: Application No. PCT/EP2014/058199; citing: WO 2013/026012 A1, US 2011/071508 A1, US 2009/054909 A1, US 2002/143319 A1.

*Primary Examiner* — Ryan N Henderson
*Assistant Examiner* — Pamela F Wu
(74) *Attorney, Agent, or Firm* — Cantor Colburn LLP

(57) ABSTRACT

A robot configured for mini-invasive surgery through a single parietal incision and/or natural orifice includes at least one articulated support, a stiffening component, and at least one maneuvering element. The articulated support includes a plurality of rigid bodies that are mutually associated. The stiffening component is associated with the articulated support and adapted for the transition of the articulated support from an inactive configuration, in which the rigid bodies can move with respect to each other, to an active configuration, in which the rigid bodies are mutually aligned so as to form a guide, and vice versa. The least one maneuvering element can be associated slidingly with the guide of the articulated body in its active configuration and can engage selectively a plurality of operating instruments accommodated in at (Continued)

least one container body that can be associated with the articulated support in its active configuration.

7 Claims, 23 Drawing Sheets

(51) Int. Cl.
    *A61B 90/35*     (2016.01)
    *A61B 1/00*     (2006.01)
    *A61B 17/00*     (2006.01)
    *A61B 90/00*     (2016.01)
    *A61B 90/30*     (2016.01)
    *A61B 90/11*     (2016.01)

(52) U.S. Cl.
    CPC .......... *A61B 1/00149* (2013.01); *A61B 90/35* (2016.02); *A61B 90/11* (2016.02); *A61B 90/30* (2016.02); *A61B 90/361* (2016.02); *A61B 2017/00477* (2013.01); *A61B 2034/302* (2016.02); *A61B 2034/306* (2016.02)

(58) Field of Classification Search
    CPC ........ A61B 2034/304; A61B 2034/305; A61B 2034/306; A61B 34/32; A61B 34/35; A61B 34/37; A61B 34/71; A61B 34/72; A61B 34/73; A61B 2034/715; A61B 2034/731; A61B 2034/732; A61B 2034/733; A61B 34/75; A61B 34/76; A61B 34/77; A61B 1/00131; A61B 1/00133; A61B 1/00147; A61B 1/00149; A61B 1/0016; A61B 1/0057; A61B 1/008; A61B 1/01; A61B 2034/301–306; A61B 34/70–77
    USPC ....... 600/102, 104, 109, 112, 114, 121, 123, 600/127–131, 136–150, 160, 164, 172, 600/175–176
    See application file for complete search history.

(56) References Cited

U.S. PATENT DOCUMENTS

| | | |
|---|---|---|
| 2011/0071508 A1 | 3/2011 | Duval et al. |
| 2013/0012821 A1* | 1/2013 | Lin ........................ A61B 34/73 600/473 |
| 2013/0345717 A1* | 12/2013 | Markvicka ............ A61B 34/30 606/130 |

* cited by examiner

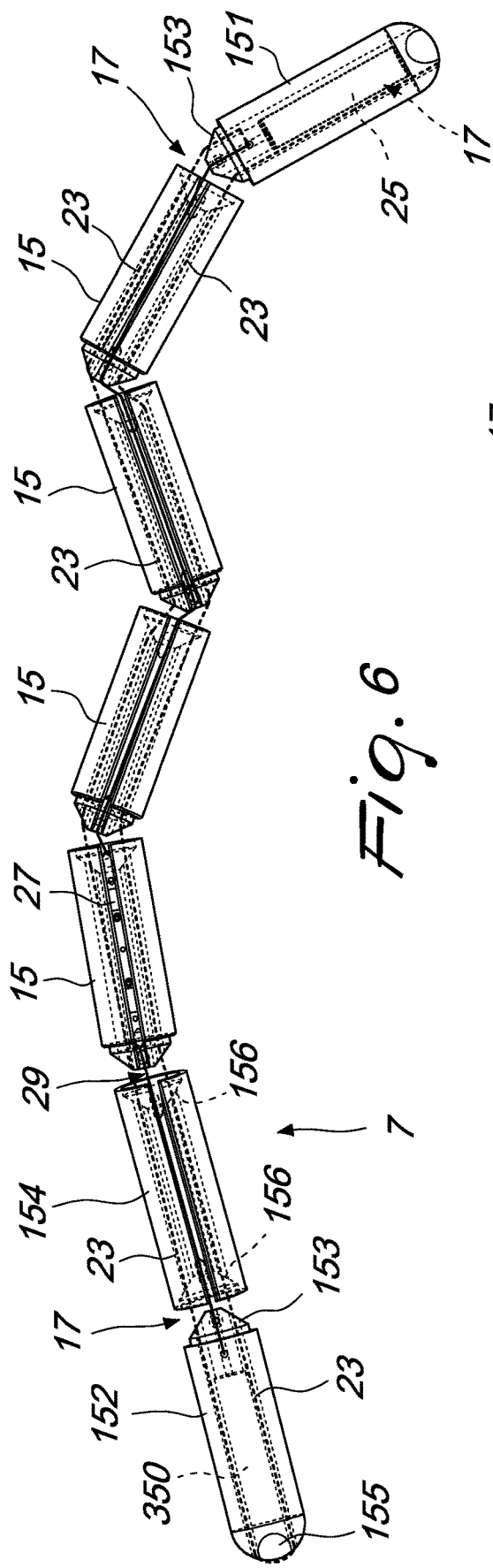
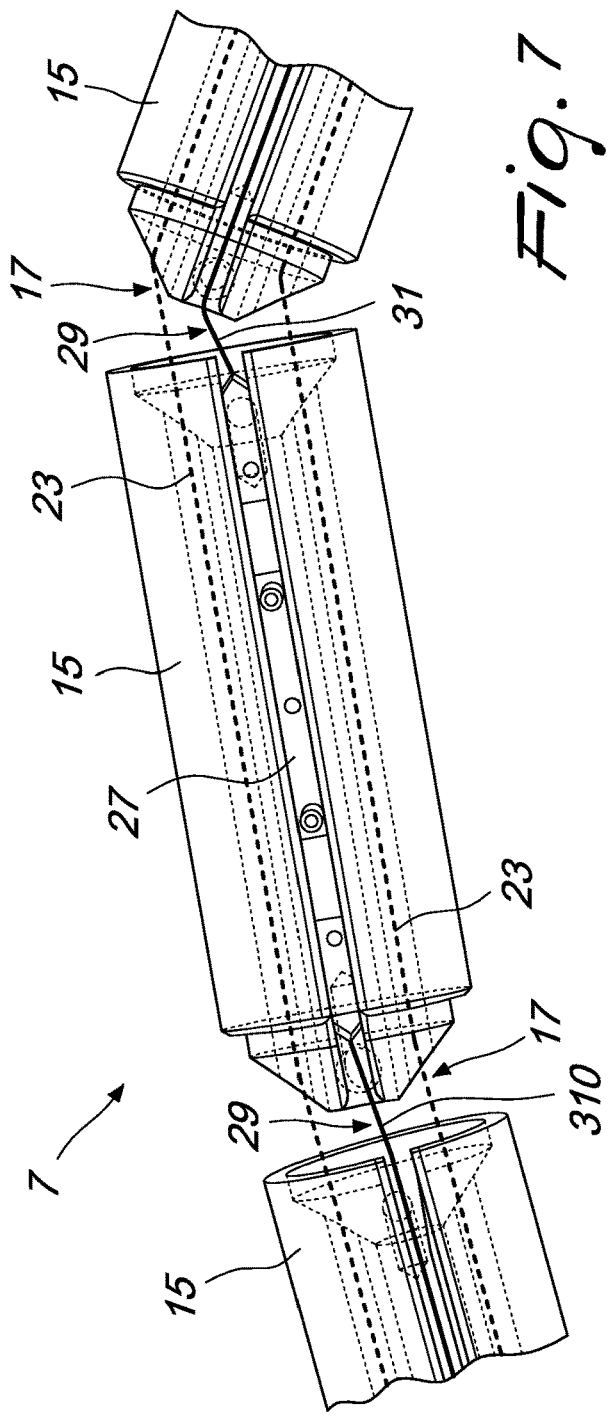

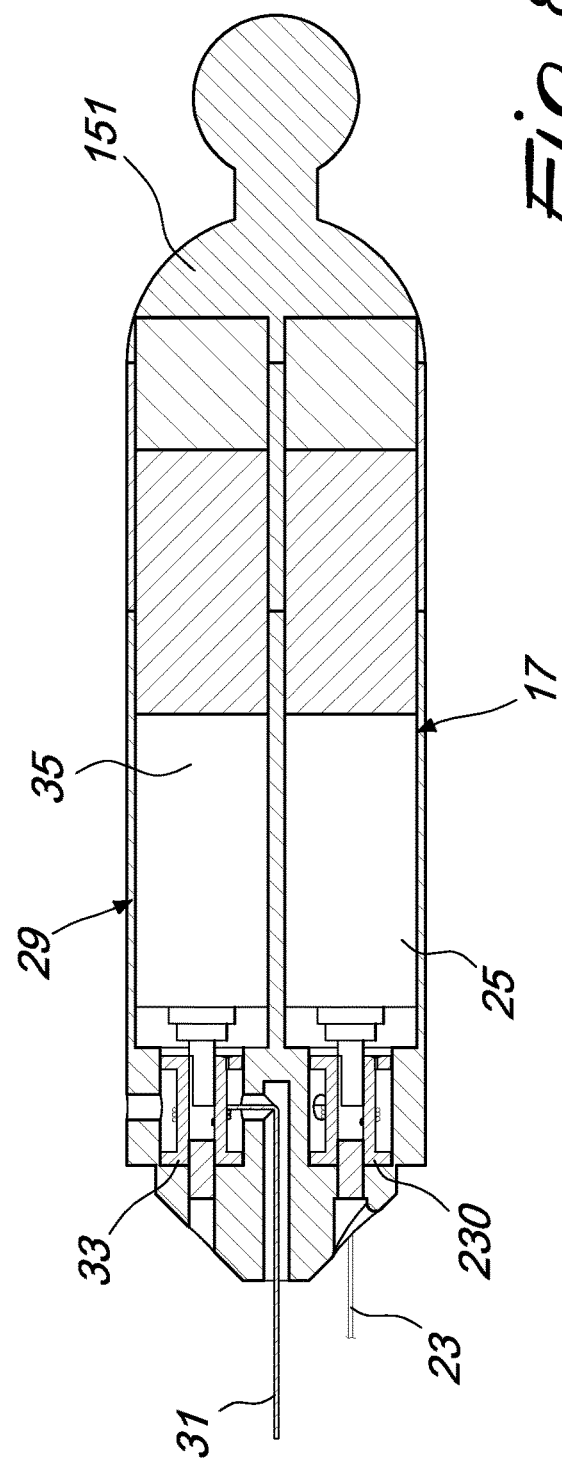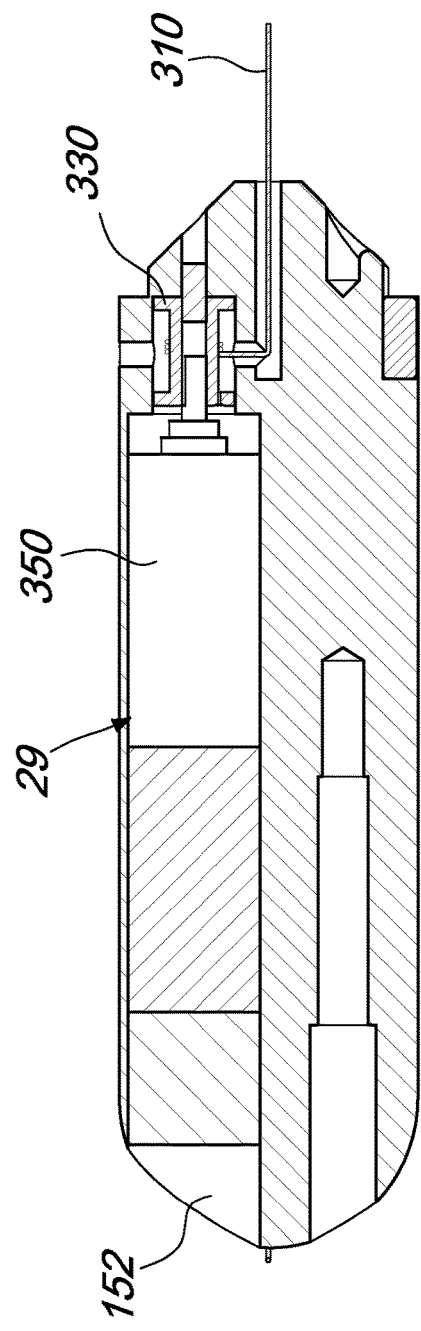

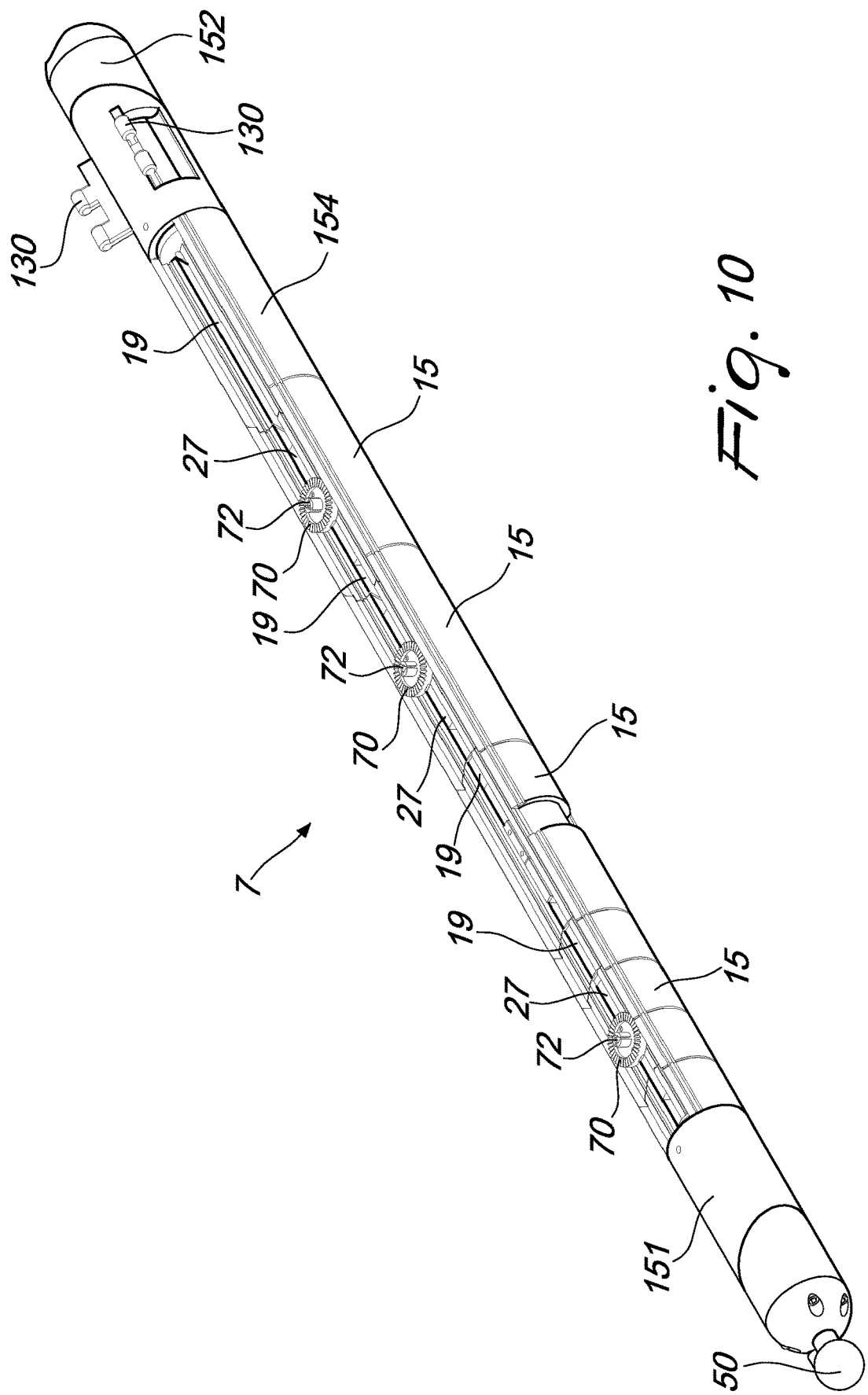

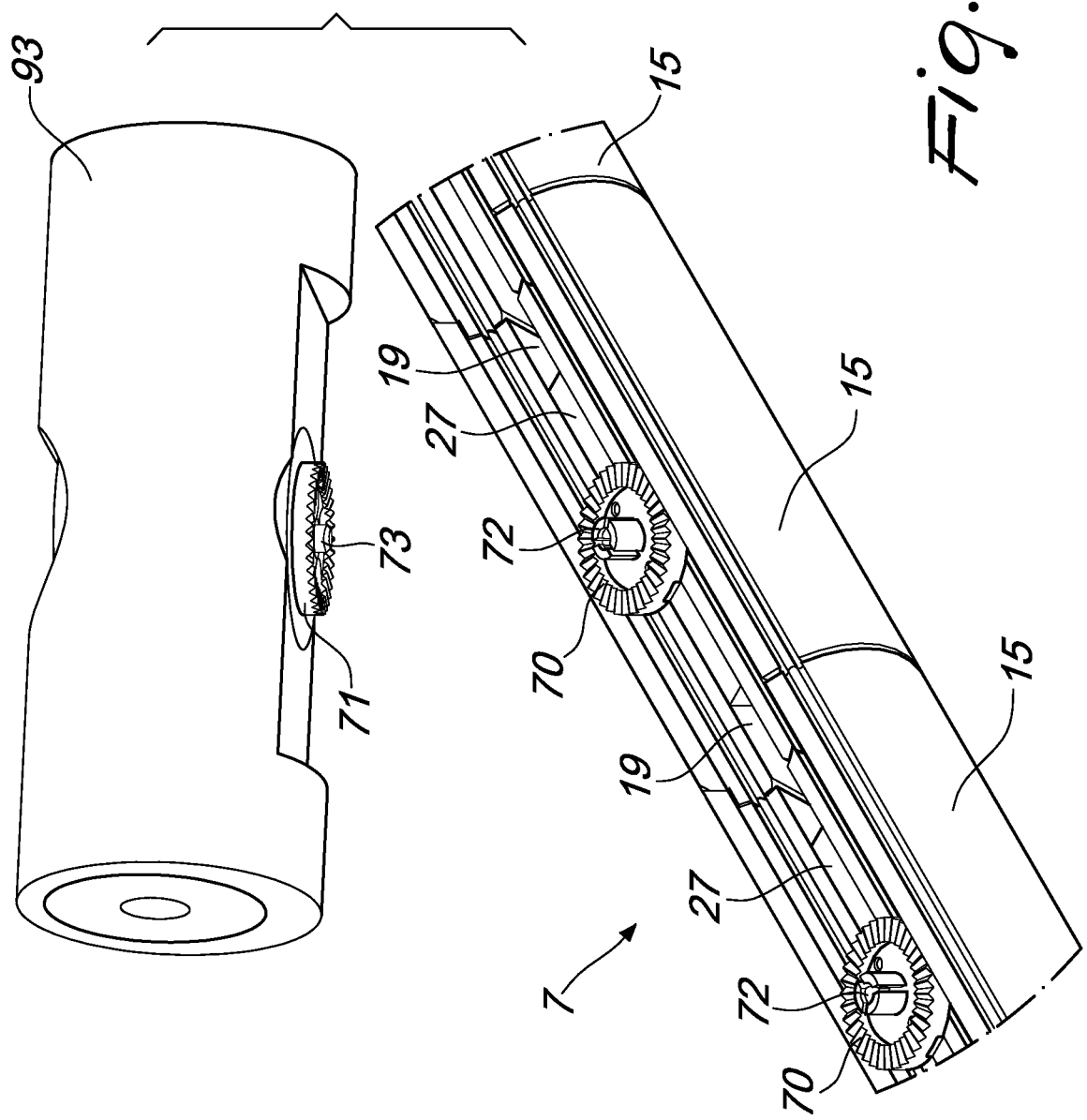

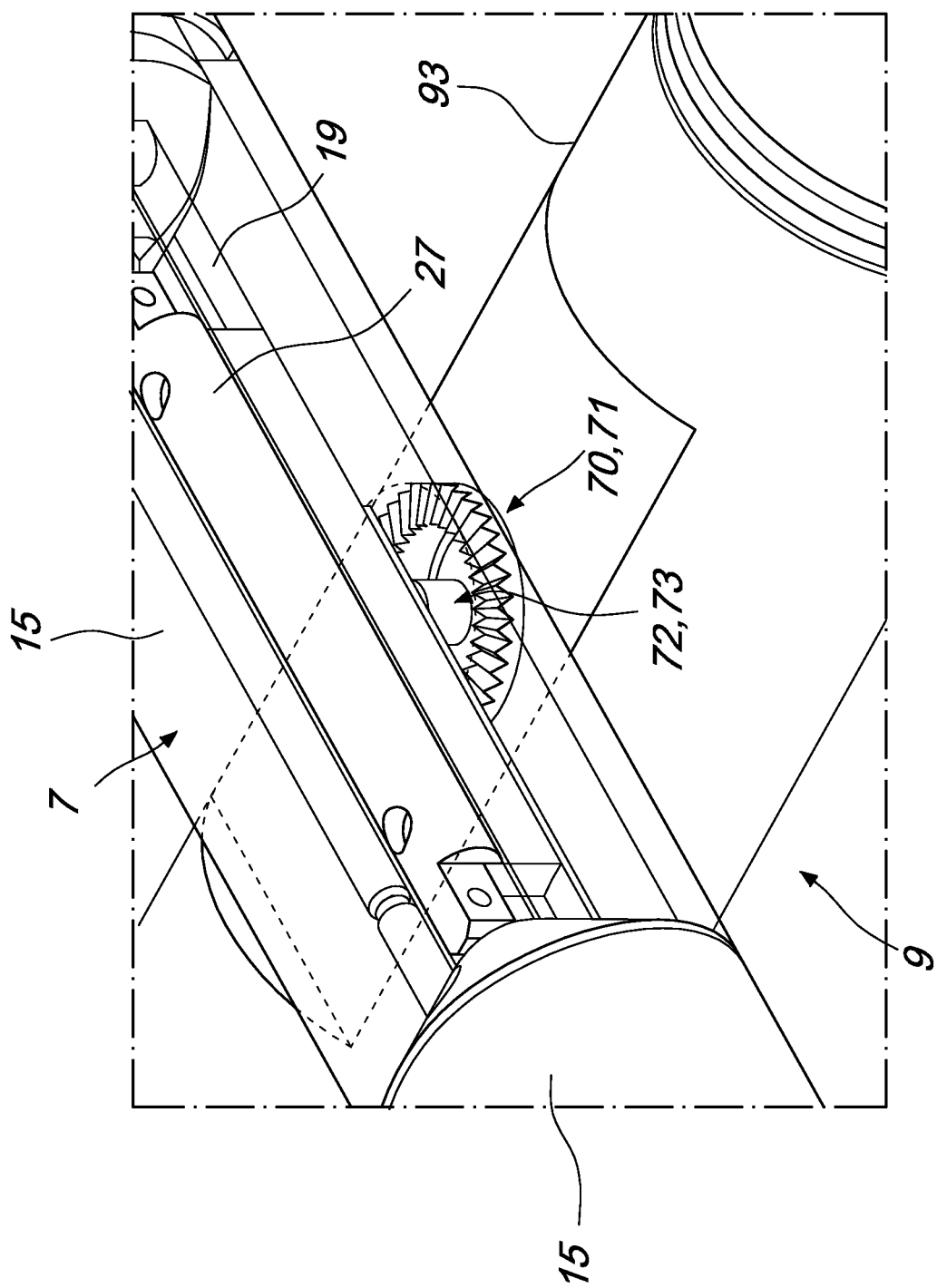

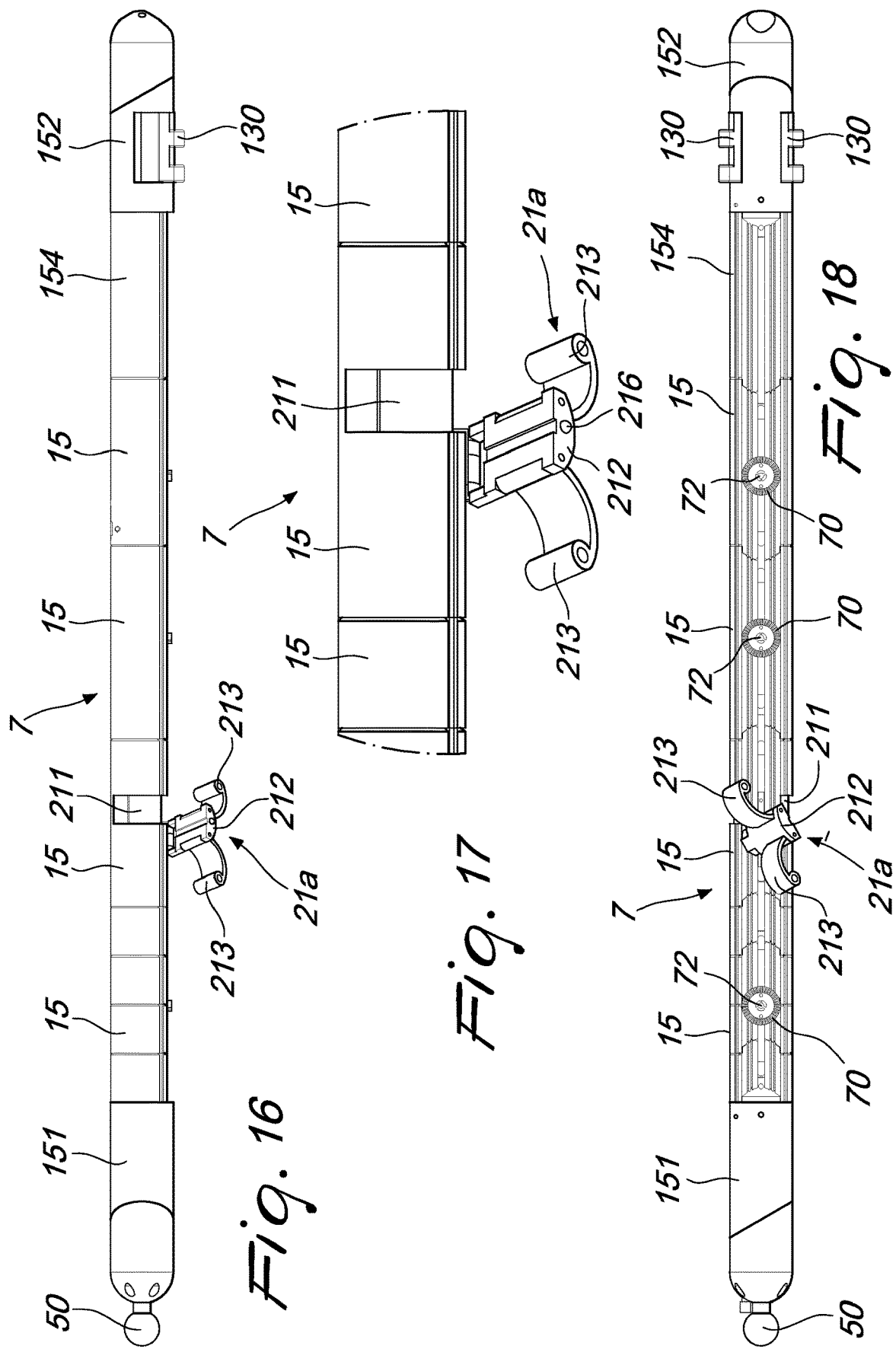

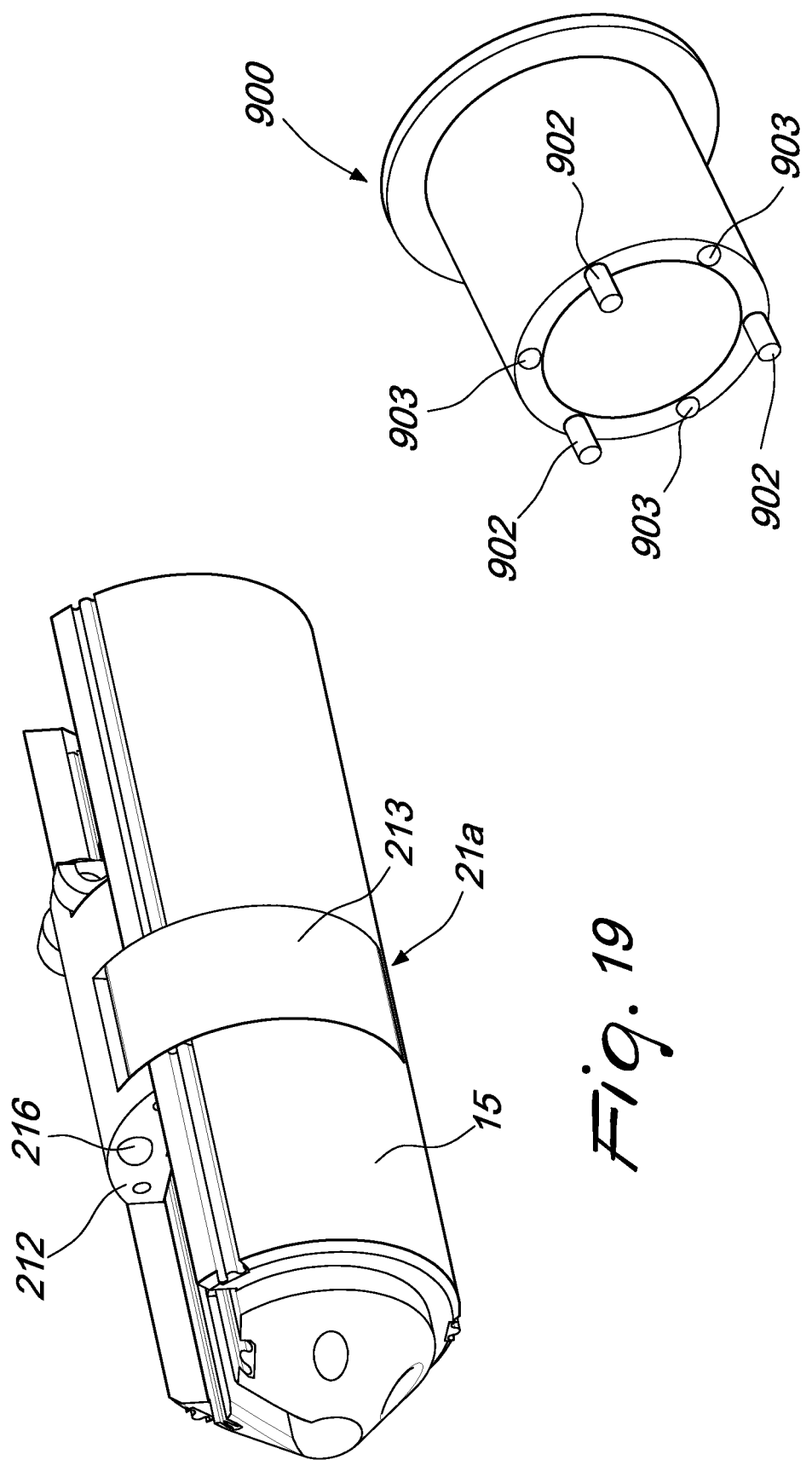

# ROBOT, PARTICULARLY FOR MINI-INVASIVE SURGERY THROUGH A SINGLE PARIETAL INCISION OR NATURAL ORIFICE

FIELD

The present disclosure relates to a robot, particularly for mini-invasive surgery through a single parietal incision or natural orifice.

BACKGROUND

The use of mini-invasive techniques has become the standard for many routine surgical procedures. However, among mini-invasive surgical techniques, laparoscopy procedures have great drawbacks, which include difficulties in accessing the surgical target and the technical limitations of working with coaxial surgical instruments. These limitations are particularly clear when one operates through a single parietal access opening (single incision) and/or natural orifice in the patient. This surgical technique imposes constrains on the possibility of triangulating the instruments, applying offset forces, and on the dimensions of the instruments themselves. Moreover, collisions often occur among instruments both inside and outside the operating surgical area. However, the use of additional surgical openings, which would allow better operability of the instruments in the surgical area, is associated with an increased risk of bleeding, for example at the level of the abdominal wall in the case of abdominal surgery, and of accidental damage of the viscera, as well as consequent increases in postoperative pain and risks of infection and formation of incisional hernias.

Conventional robotic systems for laparoscopic surgery are particularly bulky, complicated to assemble and difficult to insert and remove from the surgical area. Moreover, these robotic systems have highly limited functionalities when used in the configuration with single parietal access, and it is moreover impossible to use them through natural orifices.

SUMMARY

The present disclosure provides a robot, particularly for mini-invasive surgery, that solves the technical problems described above, obviates the drawbacks and overcomes the limitations of the background art, allowing to operate efficiently in surgical areas accessible via a single parietal opening and/or natural orifice, reducing the complications and discomfort for the patient.

Within the scope of this aim, the disclosure provides a robot that is completely functional in vivo, provides more flexibility and operative dexterity, as well as better ability to view the surgical area of interest.

The disclosure provides a robot that is highly stable in the operating configuration and therefore is capable of transmitting forces, moments and speeds of execution that are necessary for performing specific surgical operations within the surgical area, allowing at the same time a flexible and advantageous orientation of the operating instruments.

The disclosure provides a robot that allows simultaneously using different operating instruments, without requiring incisions for additional accesses to the surgical area of interest.

The disclosure provides a robot that does not require the full or partial extraction from the surgical area of the operating instruments in order to use different operating terminals assigned to different surgical actions.

The disclosure further provides a robot that can provide an integrated and three-dimensional view of the operating field as well as the necessary lightning, without the need for additional abdominal openings or incisions.

The disclosure provides a robot that can be inserted easily, through a single parietal access opening and/or natural orifice, in the surgical area of interest.

Additionally, the disclosure provides a robot that is suitable to perform, in the surgical area of interest, such as for example but not exclusively the peritoneal cavity, a plurality of operations such as, for example operations for suturing, handling of tissues, cauterization, irrigation/lavage of the operating field, and aspiration of liquids.

Moreover, the disclosure provides a robot that can be operated remotely, using a control console arranged in the operating room and/or outside it.

The disclosure also provides a robot that is capable of giving the greatest assurances of reliability and safety in use.

The disclosure further provides a robot that is easy to provide and use and is economically competitive if compared with the background art.

This aim and others will become better apparent hereinafter by providing a robot, particularly for mini-invasive surgery through a single parietal incision or natural orifice, comprising:
- at least one articulated support, which comprises a plurality of rigid bodies that are mutually associated;
- stiffening means, which are associated with said articulated support and are adapted for the transition of said articulated support from a rest configuration, in which said rigid bodies can move with respect to each other, to an active configuration, in which said rigid bodies are mutually aligned so as to form a guide, and vice versa;
- at least one maneuvering means, which can be associated slidingly with said guide of said articulated body in said active configuration and can engage selectively a plurality of operating instruments accommodated in at least one container body that can be associated with said articulated support in said active configuration.

BRIEF DESCRIPTION OF THE DRAWINGS

Further characteristics and advantages will become better apparent from the description of an embodiment of a robot, particularly for mini-invasive surgery, illustrated by way of non-limiting example with the aid of the accompanying drawings, wherein:

FIG. 6 is a top view of the articulated support of FIG. 2, in an inactive rest configuration;

FIG. 7 is an enlarged-scale view of a detail of the articulated support of FIG. 6;

FIG. 8 and FIG. 9 are lateral views of the terminal rigid bodies that compose the articulated support of FIG. 6;

FIG. 10 is a perspective view of the articulated support of FIG. 2, in which the lower part of the support itself can be seen, in the active configuration, with the guide in which the guiding carriages slide;

FIG. 11 is an enlarged-scale view of a portion of the articulated support of FIG. 10, which shows in particular the components of the system for fixing the maneuvering means to the articulated support;

FIG. 12 is a perspective view of a detail of the system for fixing the maneuvering means to the articulated support;

FIG. 16 is a side view of the articulated arm, showing a variation of the viewing means of FIG. 14, in the open active configuration;

FIG. 17 is an enlarged-scale view of a portion of the articulated support of FIG. 16, which shows in particular the viewing means in the open active configuration;

FIG. 18 is a bottom view of the articulated arm of FIG. 16, with the viewing means in the open active configuration;

FIG. 19 is an enlarged-scale view of a portion of the articulated support of FIG. 16, showing in particular the viewing means, in the closed configuration;

FIG. 23 is a view of the terminal portion of a trocar used to access the surgical area;

DETAILED DESCRIPTION OF THE DRAWINGS

Figure 1:
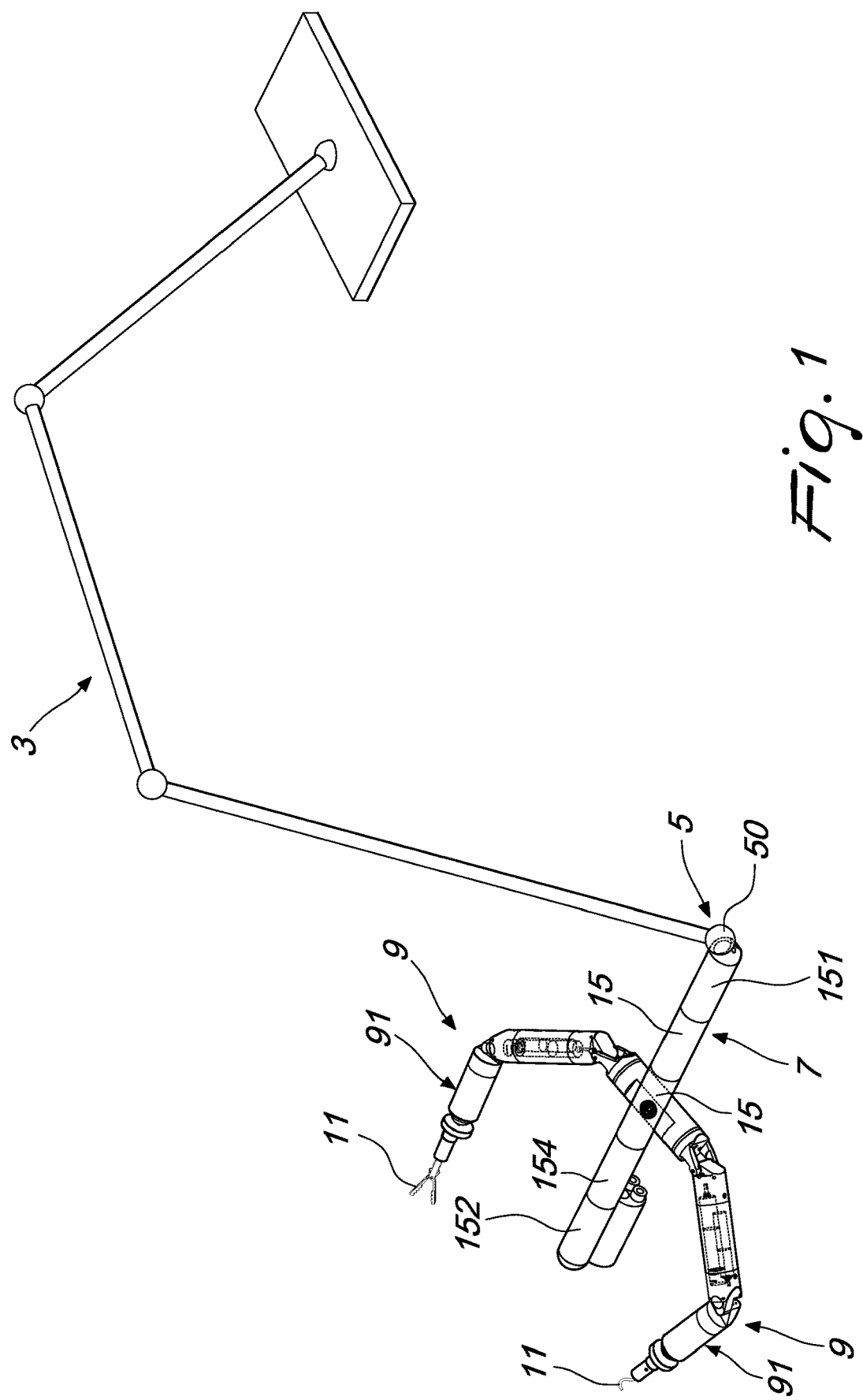
FIG. 1 is a general perspective view of an embodiment of a robot, according to the disclosure.
Figure 2:
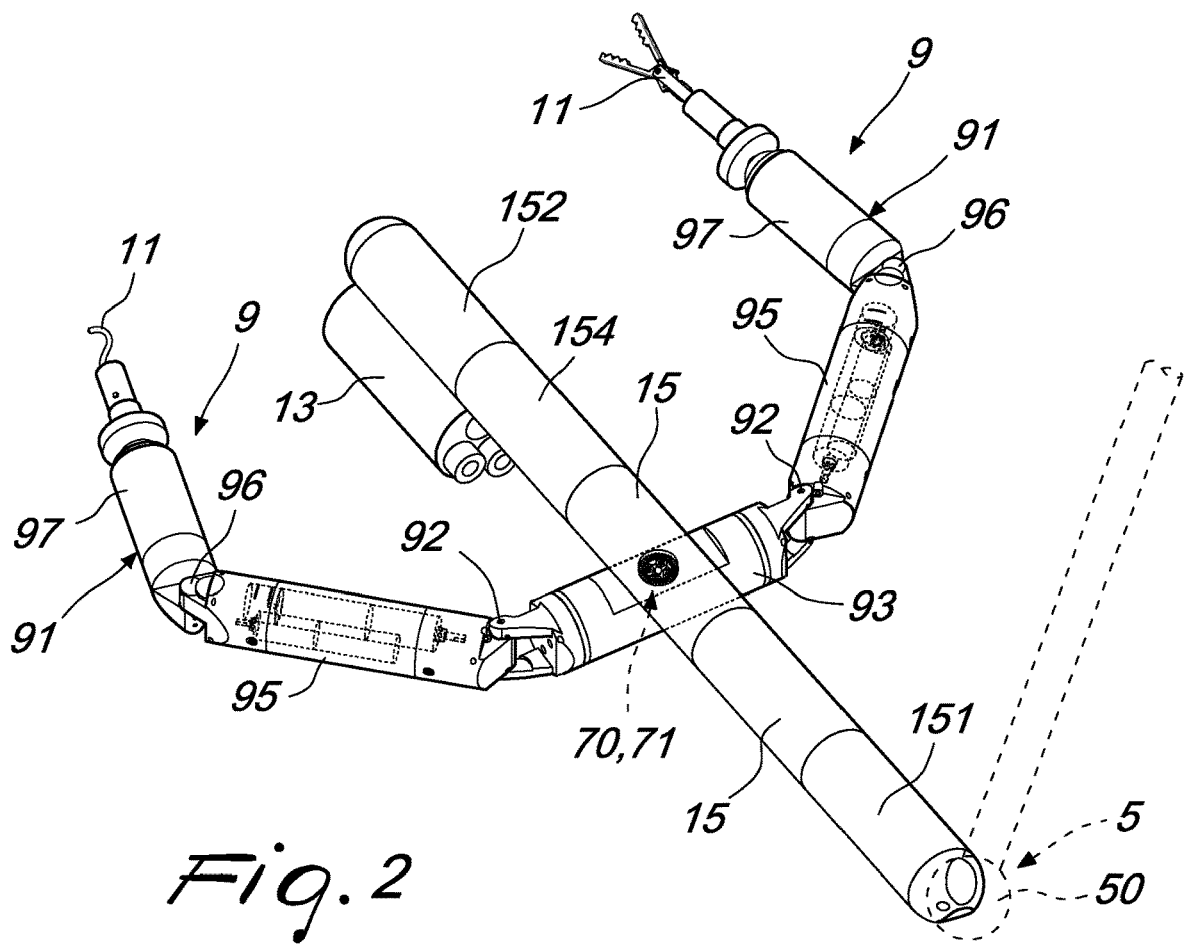
FIG. 2 is a perspective view of the robot in FIG. 1, according to the disclosure, showing in particular the articulated support, the maneuvering means with the corresponding operating instruments and the container body of the operating instruments.
Figure 3:
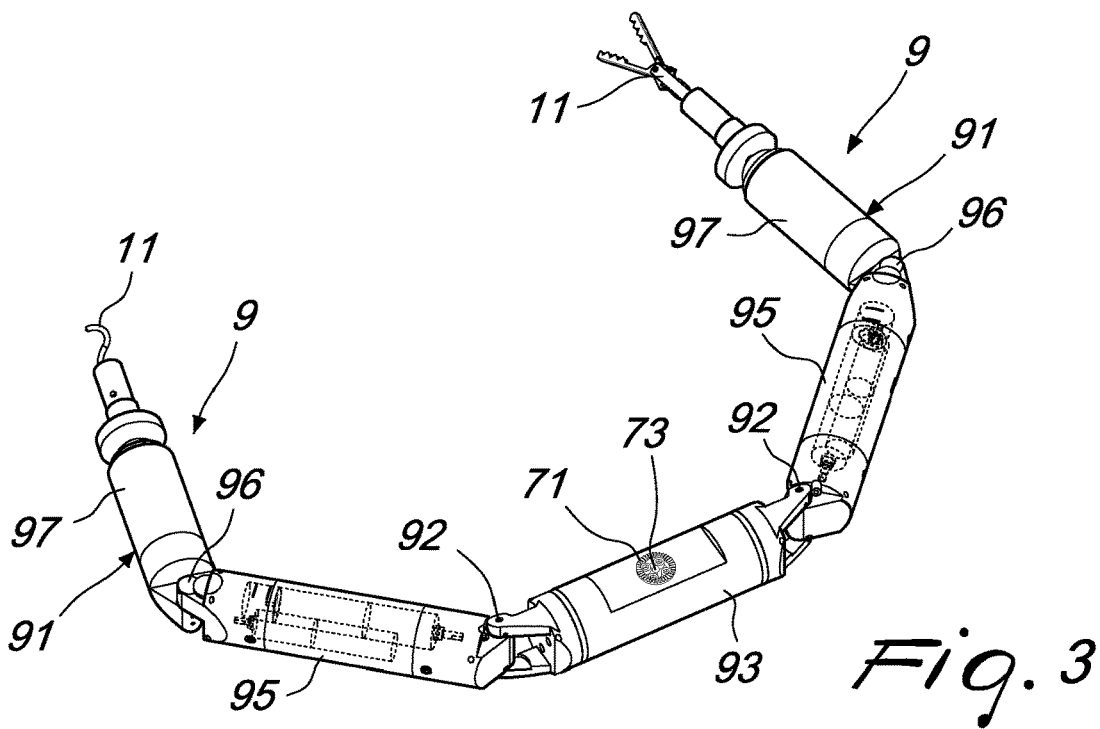
FIG. 3 is a perspective view of the maneuvering means with the corresponding operating instruments, shown in FIG. 2.
Figure 5:
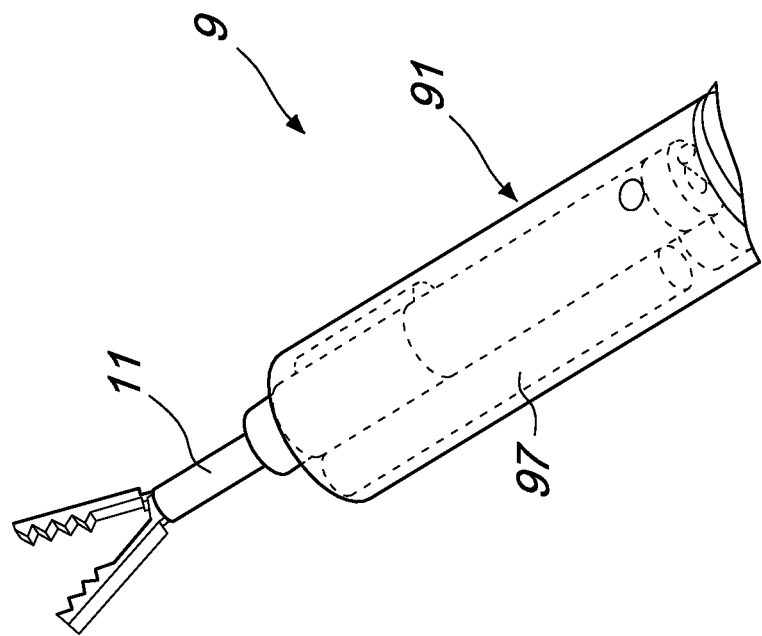
FIG. 5 is a perspective view of the end part of the maneuvering means of FIG. 3, to which an operating instrument is engaged.
Figure 4:
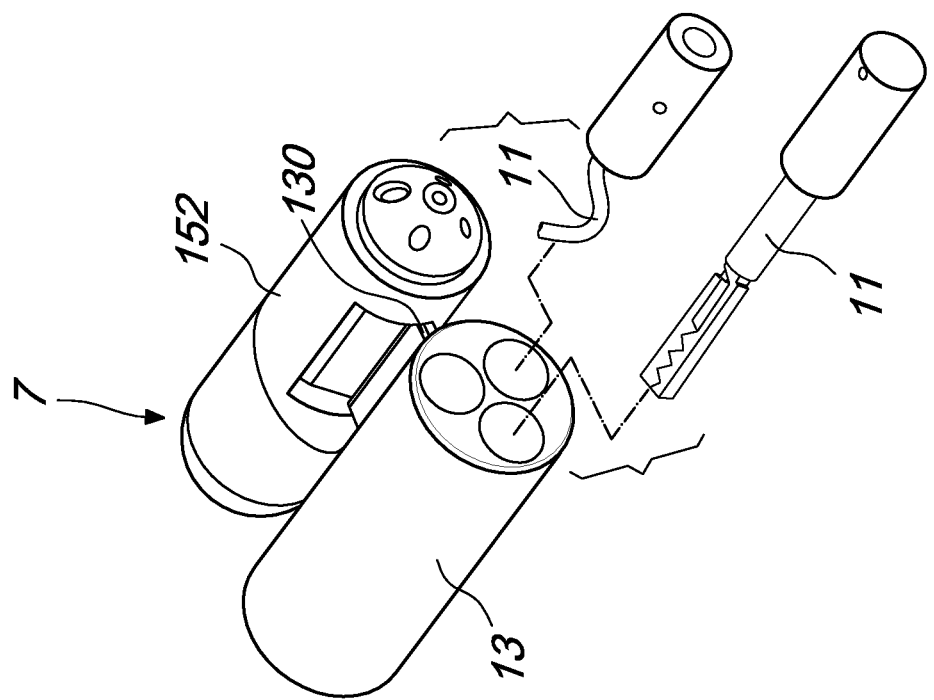
FIG. 4 is a perspective view of a portion of the articulated support of FIG. 3, to which a container body that contains two different operating instruments is engaged.
Figure 13:
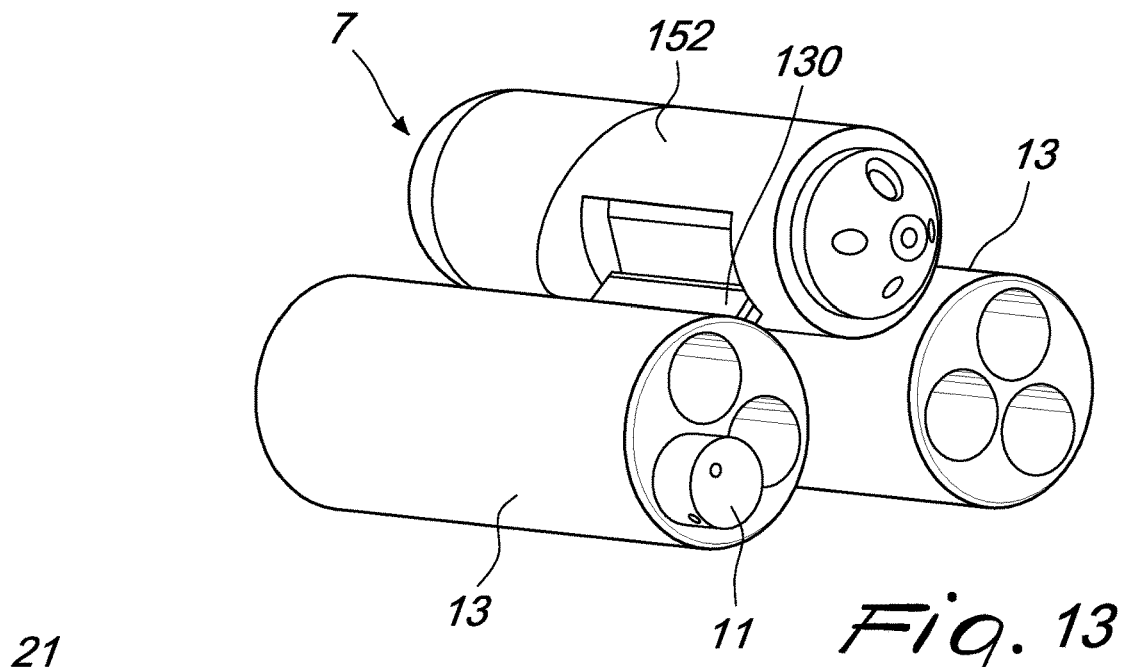
FIG. 13 is a perspective view of the portion of the articulated support shown in FIG. 4, provided with two container bodies.

With reference to the cited figures, the robot, particularly for mini-invasive surgery, is generally designated by the reference numeral 1.

According to the disclosure, the robot 1 comprises:

at least one articulated support 7, 107, which comprises a plurality of rigid bodies 15, 151, 152, 154, 115, 251, 252, 254 that are mutually associated;

stiffening means 17, 117, which are associated with the articulated support 7, 107 and are adapted for the transition of the articulated support 7, 107 from a rest configuration, in which the rigid bodies 15, 151, 152, 154, 115, 251, 252, 254 can move with respect to each other, to an active configuration, in which the rigid bodies 15, 151, 152, 154,115, 251, 252, 254 are mutually aligned so as to form a guide 19, and vice versa;

at least one maneuvering means 9, which can be associated slidingly with the guide 19, 119 of the articulated support 7, 107 in its active configuration and can engage selectively a plurality of operating instruments 11, 111 accommodated in at least one container body 13, 113 that can be associated with the articulated body 7, 107 in its active configuration.

Advantageously, the rigid bodies 15, 151, 152, 154,115, 251, 252, 254 mutually associated in order to form the articulated support 7, 107, in the active configuration, have a shape that is substantially elongated along a predefined direction.

However, it is also possible to provide rigid bodies which, mutually associated in the active configuration, form an articulated support that has a desired generally curvilinear shape. In this case, each rigid body may have a slightly arched shape, or may have a geometry of the mating with the adjacent rigid bodies such that two adjacent rigid bodies are not aligned but are mutually more or less inclined. This option allows the articulated support 7, 107 to better adapt to the anatomical conditions of the patients, particularly in the case of introduction of the robot 1 through natural orifices, ensuring at the same time a substantial operating stability of the robot itself.

The container body 13, 113 can be associated advantageously with an end of the articulated support 7, 107. If there are multiple container bodies 13, 113, more than one of them may be associated with an end of the articulated support 7, 107, or one or more container bodies 13, 113 may be associated with both of the ends of the articulated support 7, 107.

The container body 13 can be fixed to an end of the articulated support 7 by means of an engagement tab 130, which is arranged at the end of the articulated support 7 and is adapted to open with respect to the articulated support 7, in the active configuration, and therefore to engage stably in a corresponding engagement slot 131 formed in the container body 13. The movement of the maneuvering means 9 allows advantageously to rotate and orient the container body 13 associated therewith so that the engagement tab 130 engages the engagement slot 131.

The maneuvering means 9 are advantageously adapted to engage selectively the operating instruments 11, 111 accommodated in the container body 13, 113 directly inside the surgical area of interest; in particular, the maneuvering means 9 can engage the operating instrument 11, 111, needed to perform a specific operation, from the container body 13, 113, and then return it therein in order to engage a different operating instrument 11, 111, in order to perform a different operation.

In this regard, the container body 13, 113 can comprise safety devices adapted to ensure that the operating instruments 11, 111 are always associated alternatively with the container body 13, 113 or with the maneuvering means 9, so that no operating instrument 11, 111 can be left in the surgical area of interest and therefore be forgotten.

These safety devices can comprise bayonet systems provided with electrical contacts, capable of utilizing the rotary motions, with respect to its own longitudinal axis, of the terminal end of the maneuvering means 9, in order to engage or disengage safely the operating instruments 11, so that they are always connected to the maneuvering means 9 or to the container body 13 or possibly to both. The electrical contacts can advantageously supply feedback information about the operating instruments being fixed or not to the maneuvering means 9 or to the container body 13, or transfer the electrical signals needed in order to use the various operating instruments 11. Advantageously, the operating instruments 11 can be electrified with single-pole and/or two-pole current in order to allow the correct execution of the surgical operation.

Advantageously, the robot 1 comprises a supporting structure 3 for an adapter 5, to which the articulated support 7 can be connected according to desired positions and orientations. Advantageously, the adapter 5 is compatible mechanically with various types of supporting structure 3, such as commercially available supporting structures.

Advantageously, the supporting structure 3 is adapted to be fixed to the operating table and conveniently oriented in order to support the adapter 5 in a position that is suitable for the single-opening access chosen by the surgeon in order to reach the surgical area of interest.

The supporting structure 3 and the adapter 5 are therefore adapted to support, in a stable and rigid manner, the articulated support 7, so as to maintain the position of the articulated support 7 and of the maneuvering means 9 associated therewith in the desired position and orientation within the surgical area, during the operation.

The connection between the adapter 5 and the articulated support 7 is provided advantageously by a spherical hinge 50, which in the active configuration of the robot 1 can be rendered rigid.

The supporting structure 3, which is advantageously constituted by a plurality of articulated rigid segments, can be conveniently moved and oriented proximate to the opening for access to the surgical area, in an initial positioning and orientation step, before being rigidly locked in a chosen position and with a chosen orientation.

Advantageously, the maneuvering means 9 comprise at least one robotic arm 91 that has at least one degree of freedom, preferably at least 4 degrees of freedom and more preferably 7 degrees of freedom. The terminal end of each robotic arm 91 engages selectively one of the operating instruments 11 contained in the container body 13.

Advantageously, the robotic arm 91 is coupled, by means of a first joint 92 of the shoulder type, to a supporting body 93 that comprises engagements systems 71 and 73, adapted to engage the corresponding engagements systems 70, 72 that are present on the articulated support 7, and particularly on the guiding carriage 27, which can slide in the guide 19 of said articulated support 7. A first segment 95, which constitutes the arm of the maneuvering means 9, is articulated to the first joint 92. A second segment 97, which constitutes the forearm of the maneuvering means 9, is articulated, by means of a second joint 96 of the elbow type, to said first segment 95. An operating instrument 11 is articulated to the second segment 97 of the robotic arm 91, for example by means of a third joint, preferably of the wrist type. The segments of the robotic arm 91 can be actuated by motor means, such as micro-motors, conveniently inserted in the robotic arm 91 itself, for example in the supporting body 93, or in one or more of the segments 95 and 97.

Advantageously, the maneuvering means 9 can comprise two robotic arms 91, adapted to operate with two identical or different operating instruments 11, such as for example forceps, hooks, scalpels, needle holders for suture or cauterizing terminals.

The stiffening means 17, which are associated with the articulated support 7 and are adapted for the transition of the articulated support 7 from a rest configuration to an active configuration, comprise advantageously tensioning cables 23 that pass through the articulated support 7, and more specifically in each one of the rigid bodies 15, 151, 152, 154, and can be actuated by motor means 25. The active configuration of the articulated support 7 is obtained by the shape mating of a female end with a male end of two consecutive rigid bodies 15 (or 152, 154, or 154, 15, or 15, 151).

In particular, FIG. 6 shows the articulated support 7 in its flexible inactive rest configuration. The articulated support 7 of FIG. 6 comprises a plurality of rigid bodies 15 that each have a hollow conical end and a convex conical end, with the exception of the terminal rigid bodies 151 and 152, which only have a convex conical end 153. Moreover, the rigid body 154, proximate to the terminal rigid body 152, has both ends 156 that are hollow and conical ends.

The tensioning cable 23 can be wound, at one of its ends, around a pulley 230 that is keyed to the driving shaft of the motor means 25 arranged in the terminal rigid body 151. The tensioning cable 23 passes, in a first direction, through all the rigid bodies 15 and 154, than winds around guiding means 155 arranged in the terminal rigid body 152 and passes again, in a second direction that is opposite the first one, through all the rigid bodies 15 and 154 up to the terminal rigid body 151, to which it is fixed.

The actuation of the motor means 25 causes the winding of the tensioning cable 23 around the pulley 230 and therefore the mutual approach of the rigid bodies 15, 151, 152 and 154, which, because of the mutually concave and convex conical ends, mate with each other, making the articulated support 7 assume the rigid active configuration.

Advantageously, the articulated support 7 comprises at least one guiding carriage 27, shown in FIGS. 10 and 11, which can be associated with at least one between the maneuvering means 9 and the viewing means 21, and translation means 29 adapted to translate the guiding carriage 27 inside the guide 19.

Advantageously, the articulated support 7 comprises as many guiding carriages 27 as there are maneuvering means 9 and viewing means 21 comprised in the robot 1.

Advantageously, the translation means 29 comprise at least one translation cable 31, which is connected at a first end to the guiding carriage 27 and can be wound, at the opposite end, around a pulley 33 that is keyed to the driving shaft of motor means 35.

Advantageously, the translation means 29 comprise two translation cables 31, 310, which are connected respectively to the opposite ends of the guiding carriage 27. The first translation cable 31 is actuated by the motor means 35 arranged in the terminal rigid body 151. The second translation cable 310 is actuated by motor means 350 arranged in the terminal rigid body 152. The motor means 35 and 350 are actuated alternatively and in a coordination manner so as to allow the translation of the guiding carriage 27 in the guide 19, in both directions.

Like the motor means 35, the motor means 350 also actuate a driving shaft to which a pulley 330 is keyed, the end of the translation cable 310 that is opposite the end connected to the guiding carriage 27 being wound around said pulley 330.

As an alternative, the translation means 29 can comprise an electromagnetic linear actuator, which comprises a system of permanent magnets and electromagnets conveniently supplied electrically in order to determine the movement of the guiding carriages 27 inside the guide 19.

The robot 1 can comprise advantageously viewing means 21, which also can be associated slidingly with the guide 19 of the articulated body 7, for example by means of the engagement systems 71, 73 adapted to engage the guiding carriage 27. These viewing means 21 can be moved along the guide 19, independently of the movement of the maneuvering means 9, manually by an operator, by remote control or autonomously.

The viewing means 21 can comprise advantageously multiple video cameras, in order to ensure stereoscopic viewing, advantageously capable of performing pan and tilt motions, in order to provide a clear, wide and three-dimensional view of the surgical area of interest. The robot 1 comprises advantageously also lighting devices, such as LED devices.

Figure 14:
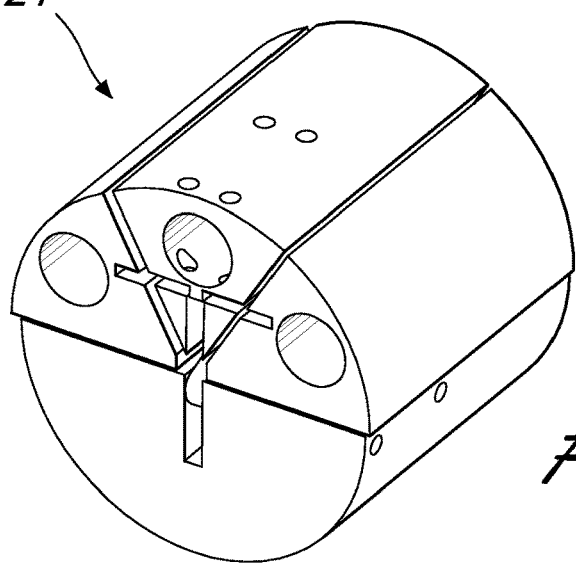
FIG. 14 is a perspective view of the viewing means of the robot, according to the disclosure, in the closed rest configuration.
Figure 15:
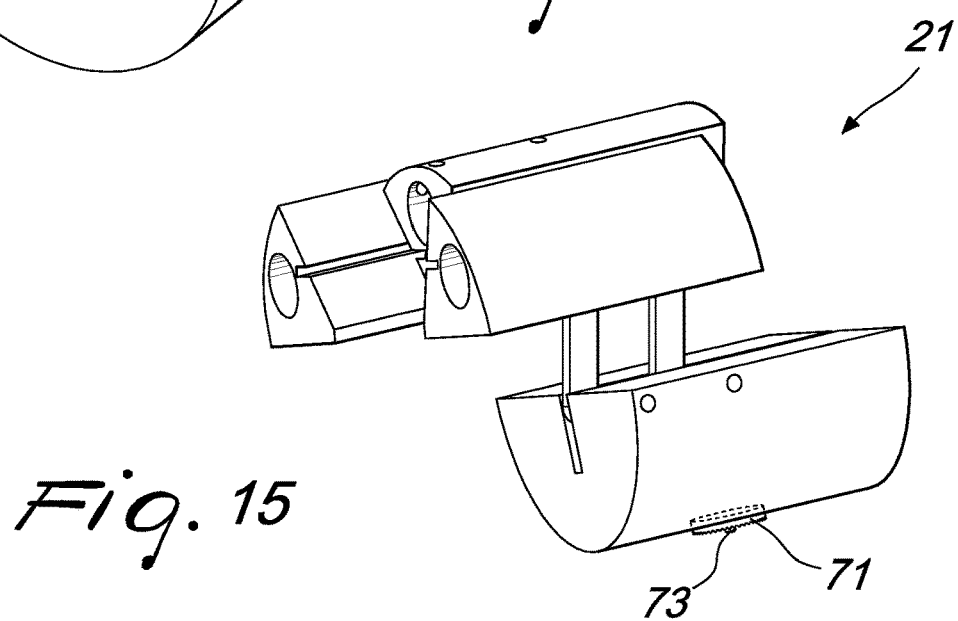
FIG. 15 is a perspective view of the viewing means of FIG. 14, in open active configuration.

The viewing means 21 have advantageously, as shown respectively in FIGS. 14 and 15, a closed rest configuration and an open active configuration, in which the video cameras are spaced so as to ensure a three-dimensional stereoscopic reconstruction of the surgical area.

In a variation of the viewing means 21a, shown in FIGS. 16, 17, 18 and 19, said viewing means 21a are incorporated inside one of the rigid bodies 15. In their closed configuration, the viewing means 21a are arranged in a suitable receptacle 211 formed in the rigid body 15, so as to remain compressed in the lateral surface of said rigid body 15 without needing any further installation procedure on the articulated support 7. In their open active configuration, the central body 212 is oriented conveniently toward the area of interest inside the surgical area, while two lateral wings 213, which contain the video cameras, open laterally, so as to allow stereoscopic viewing and recording of the imagines. The viewing means 21a can also comprise lighting devices 216, preferably integrated in the central body 212, adapted to illuminate the surgical area.

FIGS. 11 and 12 show the systems for engaging the maneuvering means 9, and particularly their supporting element 93, with the articulated support 7. In particular, the guiding carriage 27 that can slide in the guide 19 of the articulated support 7 comprises a ring element 70 adapted to engage a corresponding ring element 71 of the supporting element 93.

A blocking system is advantageously associated with this ring coupling 70, 71 and comprises an engagement pin 73 associated with the supporting body 93 and a hole 72, associated to the articulated support 7 and adapted to accommodate the engagement pin 73. This connection allows to fix stably and rigidly the maneuvering means 9 to the guiding carriage 27 at any mutual angle between the supporting element 93 and the articulated support 7. Advantageously, the supporting element 93 contains motor means adapted to actuate the ring coupling 70, 71 and the locking system 72, 73, as described hereinafter.

Advantageously, the robot 1 can comprise furthermore a plurality of maneuvering means 9, which can be associated with a plurality of operating instruments 11, as well as a plurality of container bodies 13 for said operating instruments 11, and a plurality of viewing means 21, 21a, according to the operating requirements. Said different operating modules can operate autonomously with respect to each other while ensuring the coordination needed in order to perform the operation.

According to an alternative embodiment, not shown, the tensioning cables and/or the translation cables can be actuated by motor means arranged externally with respect to the articulated support 7.

Figure 20:
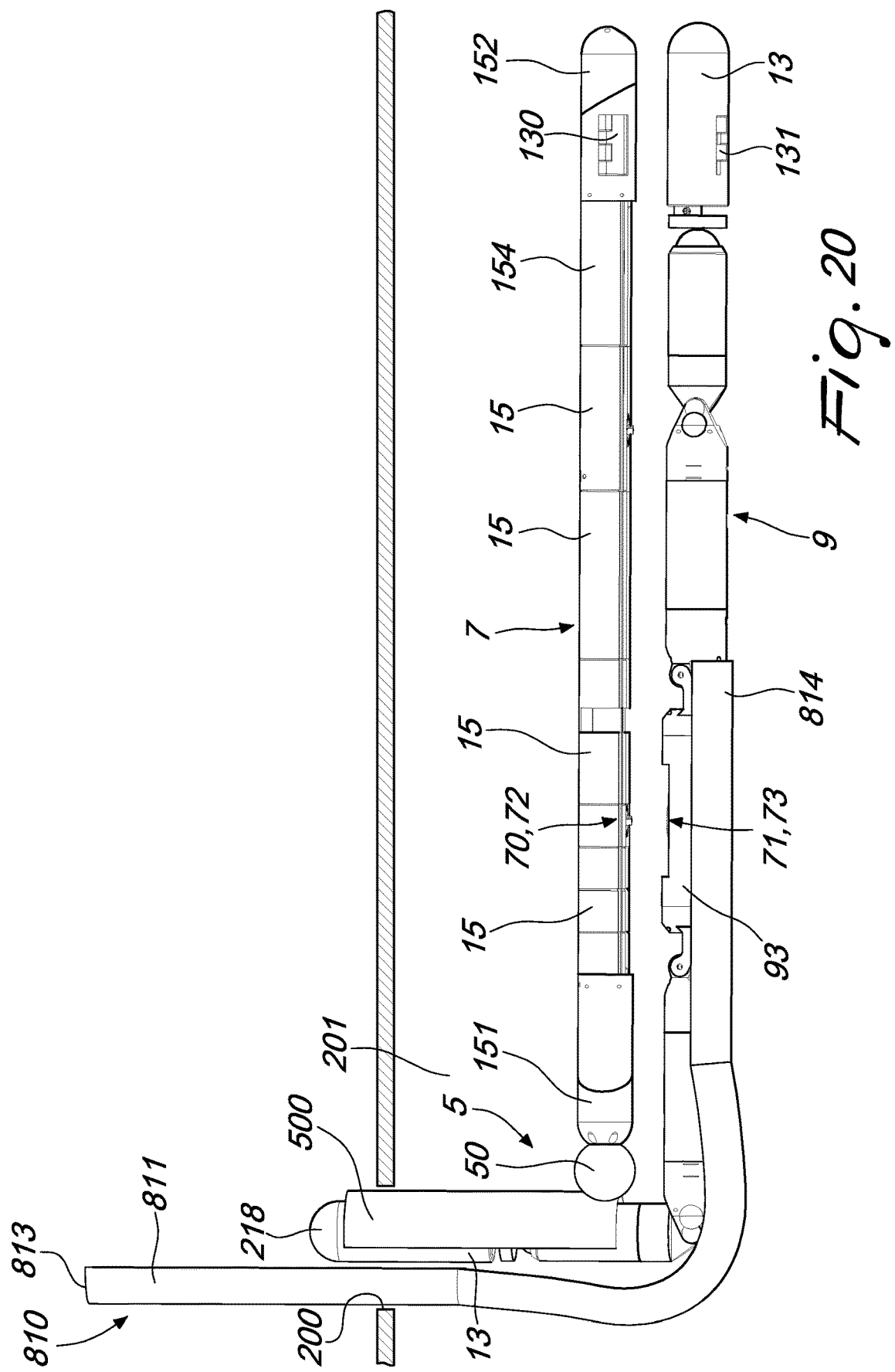
FIG. 20 is a lateral view of the articulated support and of the maneuvering means in a configuration for insertion in the surgical area, by virtue of insertion means.
Figure 21:
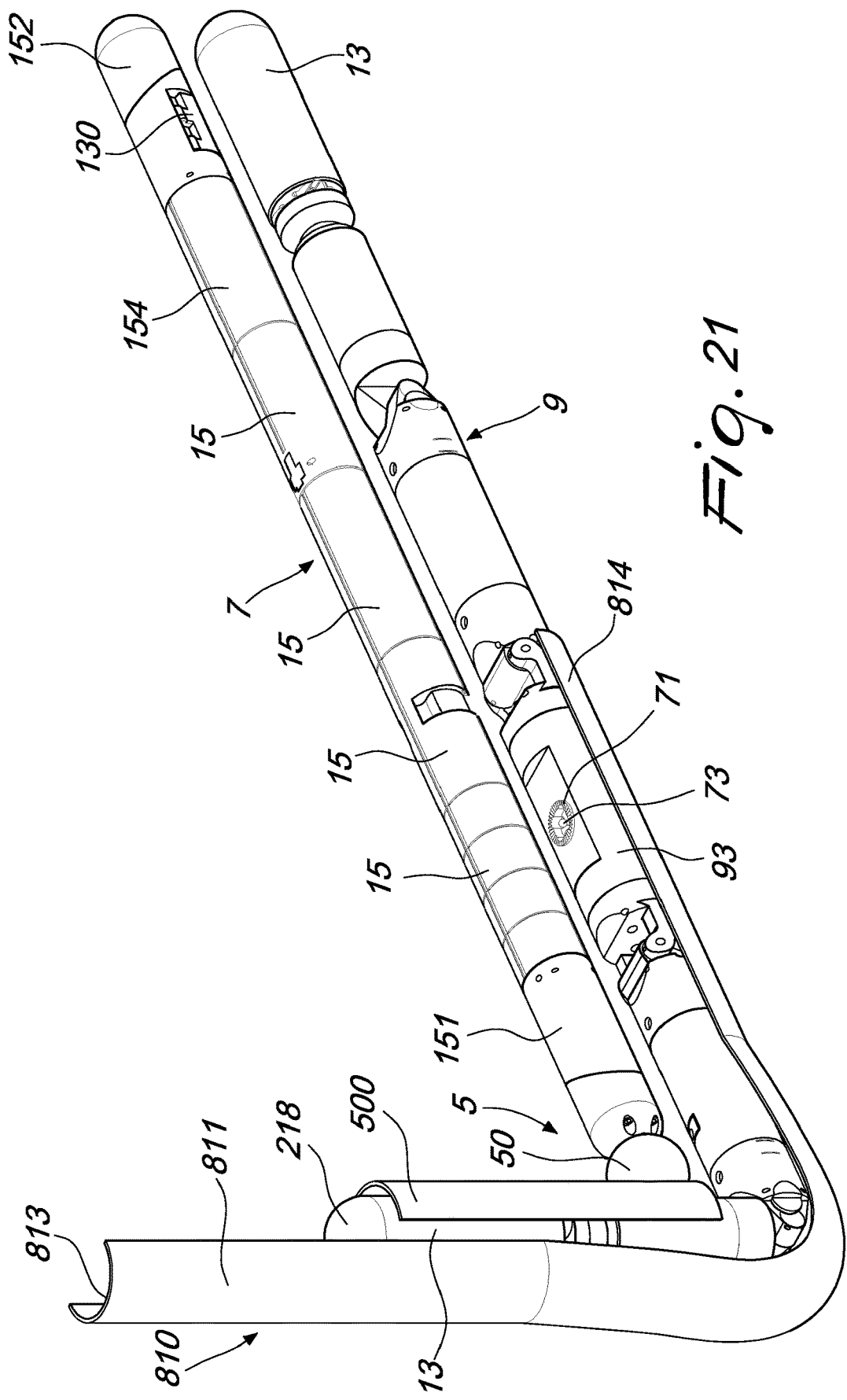
FIGS. 21 and 22 are two perspective views of the insertion means that accommodate the articulated support and the viewing means shown in FIG. 20.
Figure 22:
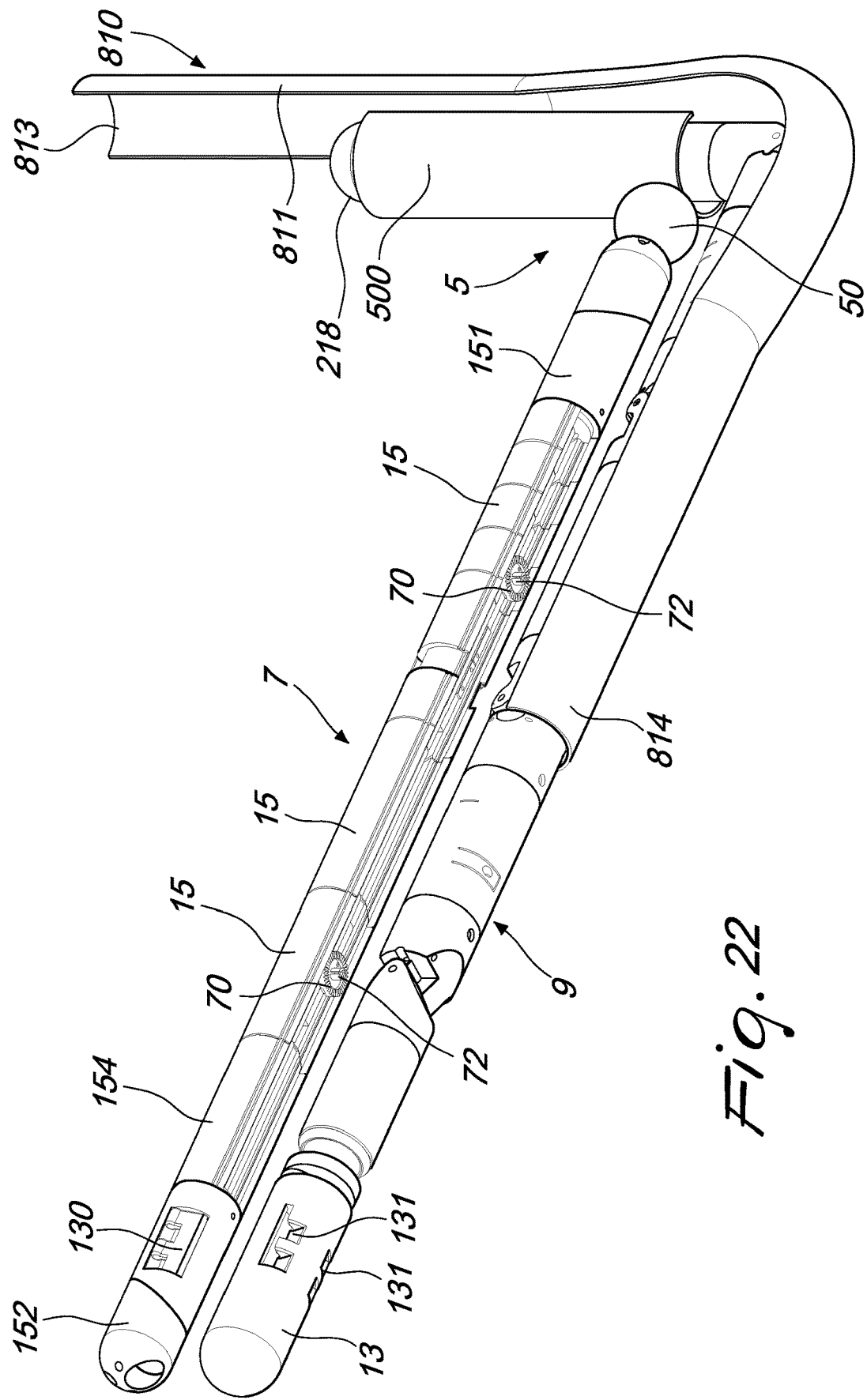

FIGS. 20, 21 and 22 show the maneuvering means 9 and the articulated support 7 during the step of insertion in the surgical area 201. This insertion occurs by virtue of the insertion means 810, which pass through the access opening 200, which is constituted by a single incision or by a natural orifice.

The insertion means 810 comprise advantageously an insertion guide 811, which is advantageously formed by a substantially tubular structure that is open on one side. This insertion guide 811 forms a substantially semicircular channel, in which the maneuvering means 9 and the articulated support 7 can slide, in their flexible rest configuration, as described hereinafter. Said insertion guide 811 advantageously has a curved shape in order to facilitate access to the surgical area 201.

As an alternative, the insertion guide 811 can be formed by a track on which the maneuvering means 9 and the articulated support 7, again in the flexible rest configuration, can engage and slide.

The insertion means 810 are intended to be arranged with respect to the access opening 200 so that one end 813 is external to the surgical area 201, and therefore accessible to the surgeon, while the opposite end 814 is arranged inside the surgical area 201.

Advantageously, as shown in FIGS. 20, 21 and 22, the adapter 5 (shown only partially) that supports the articulated support 7 can have a terminal portion 500 that has a substantially tubular structure that is open at one end. This terminal portion 500 of the adapter 5 provides a second semi-circular channel which, by facing in cooperation with the semicircular channel formed by the insertion means 810, forms, proximate to the access opening 200, a substantially circular insertion channel through which the maneuvering means 9 can be inserted in the surgical area 201, as described hereinafter.

Advantageously, the insertion guide 811 is substantially L-shaped. Moreover, said insertion guide 811 can be made of a material of the type of plastic, which can be conveniently deformed according to the requirements and the anatomy of the patient proximate to the surgical area of interest, or made of a material such as metal.

Moreover, the insertion guide 811 can be substantially rigid but have one or more flexible bending points, so that it can be shaped according to the need to access the surgical area 201.

The insertion means 810 can comprise also a mechanical retainer that prevents the further insertion of the articulated support 7 when it has been inserted to a required depth. This mechanical retainer can be conveniently actuated manually by the operator.

Figure 24:
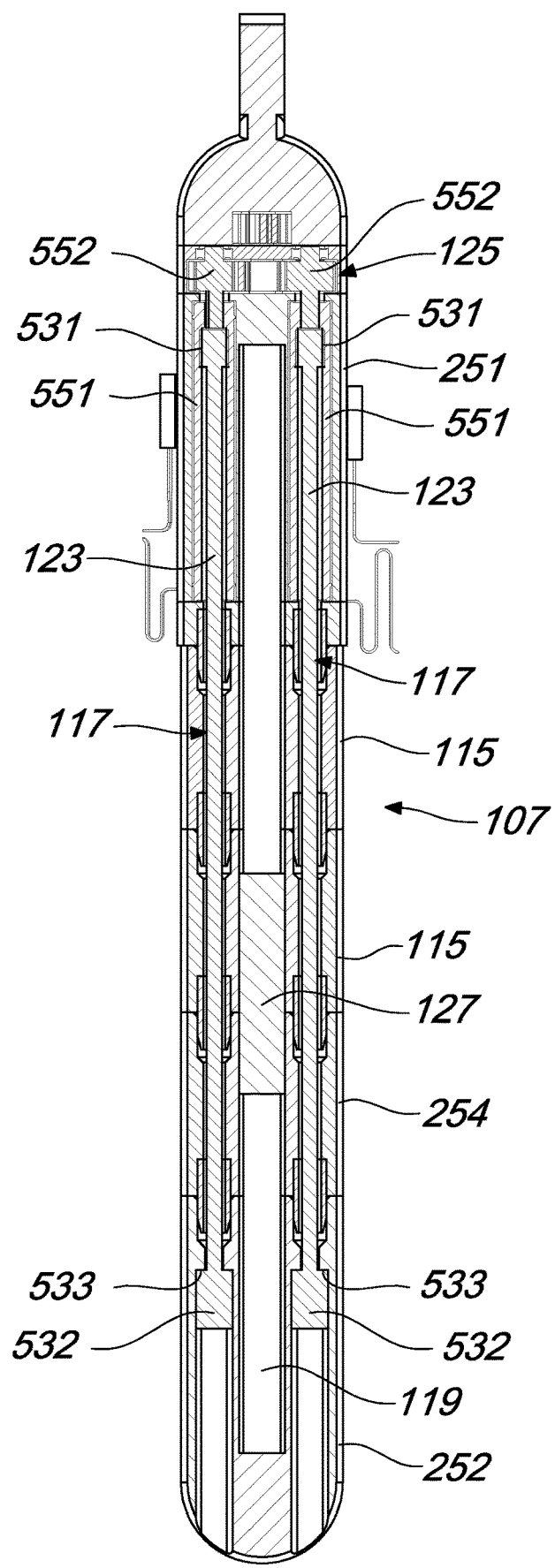
FIG. 24 is a front cross-section view of a variant of the articulated support.
Figure 25:
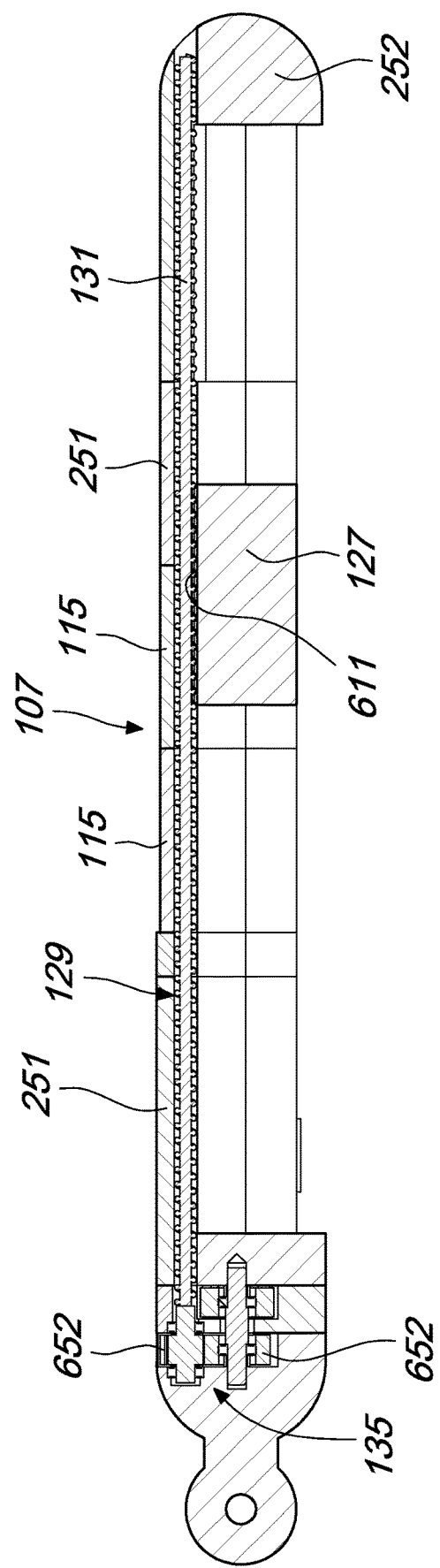
FIG. 25 is a side cross-section view of the articulated support shown in FIG. 24.
Figure 26:
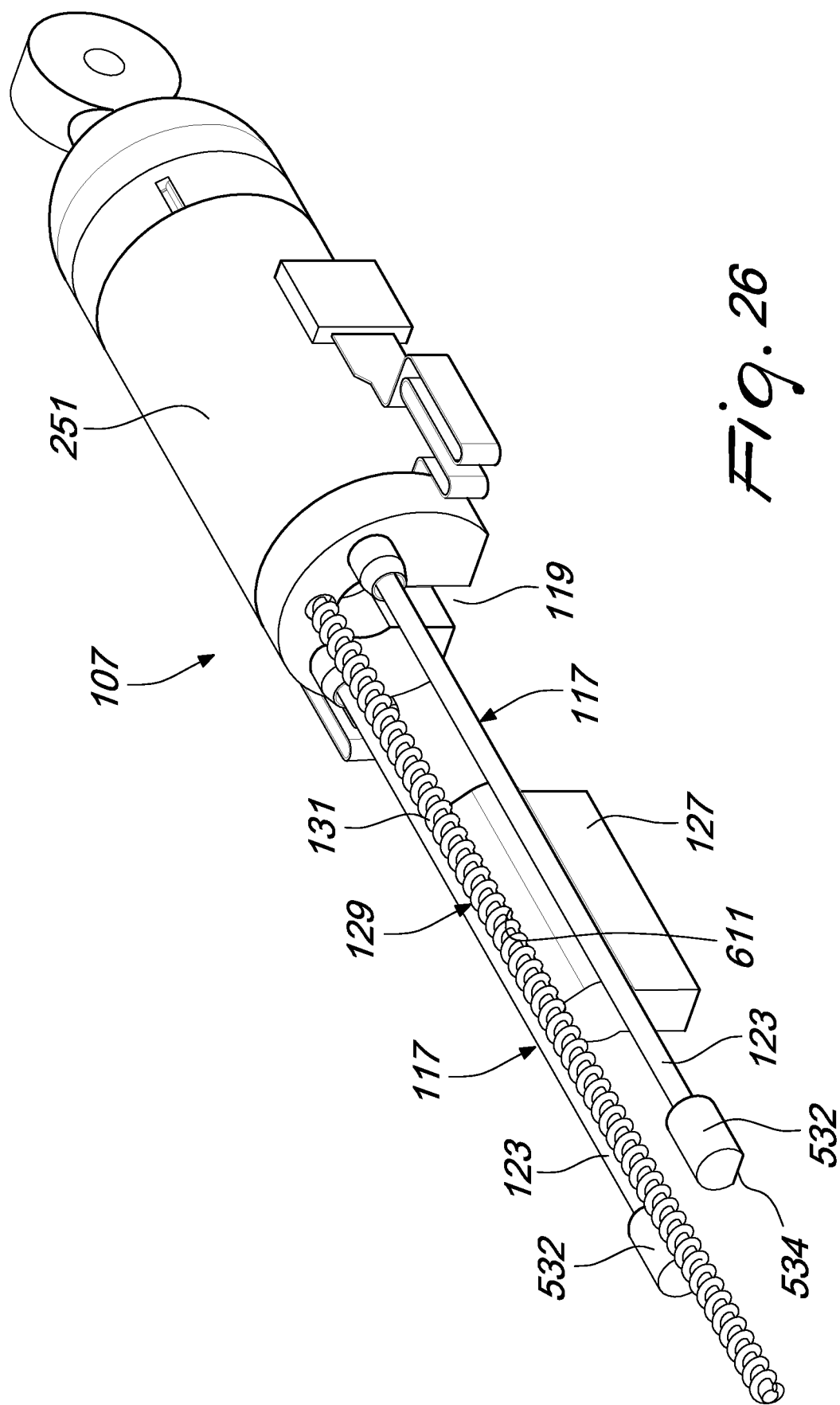
FIG. 26 is a perspective view of the articulated support shown in FIG. 24, wherein some rigid bodies have been removed.
Figure 27:
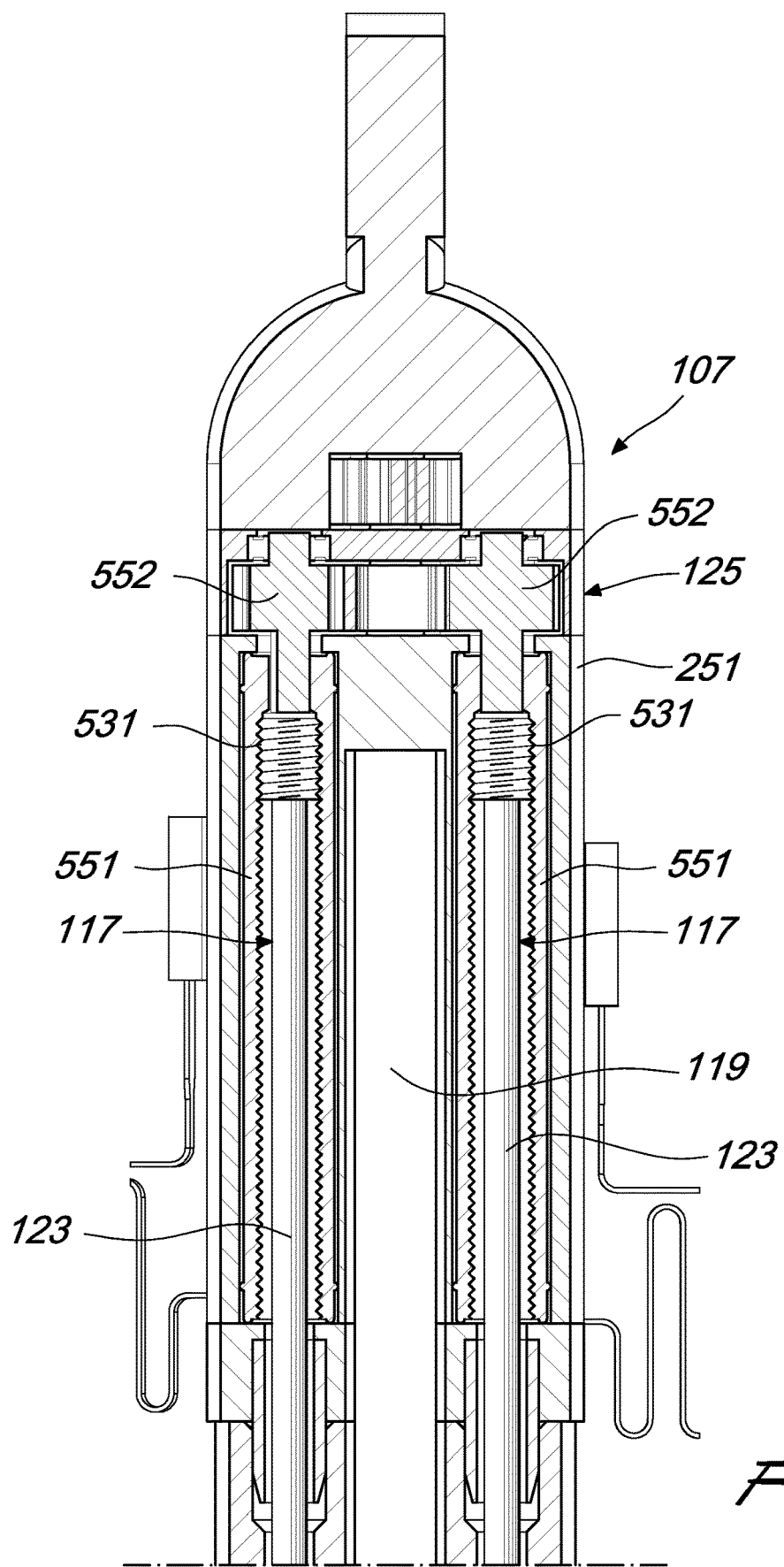
FIG. 27 is an enlarged-scale view of a portion of the articulated support of FIG. 24.

FIGS. 24, 25 and 26 show a variant of the articulated support 107. Advantageously, the articulated support 107 comprises at least one guiding carriage 127, which can be associated with at least one between the maneuvering means 9 and the viewing means 21, and translation means adapted to translate the guiding carriage 127 inside a guide 119 defined in the articulated support 107.

Advantageously, as shown in FIGS. 24, 25, 26 and 27, the stiffening means 117, which are associated with the articulated support 107 and are adapted for the transition of the articulated support 107 from a rest configuration to an active configuration, can comprise one or two tensioning elements 123 that pass through the articulated support 107, and more specifically through each one of the rigid bodies 115, 251, 252, 254. Such stiffening means 117 can be actuated by actuation means 125. The tensioning elements 123 can be tensioning cables.

The tensioning elements 123 comprise at one of their ends, a threaded body 531, and, at the opposite end, a tensioning body 532. The actuation means 125 comprise a threaded tube 551 configured to be rotated around its central axis. The threaded body 531 is configured to be moved axially within the threaded tube 551 of the actuation means 125 when the threaded tube 551 is rotated around its own axis. The actuation means 125 comprise motor means and transmission gears 552 configured to actuate the rotation of the threaded tube 551. The tensioning body 532 of the tensioning elements 123 is configured to abut against a recessed portion 533 of the rigid body 252, so that tensioning of the tensioning elements 123 results in stiffening the whole articulated support 107. Advantageously, the tensioning body 532 comprises a flat surface 534 so that any rotation of the tensioning body 532 inside the recessed portion 533 is prevented. Therefore the rotation of the threaded tube 551 results firstly in a sliding movement of the tensioning body 532 inside the recessed portion 533 of the rigid body 252 and then in the stiffening of the articulated support 107.

In FIGS. 24, 25, 26 and 27 it is also shown a variant of the translation means 129 for translating the guiding carriage 127 along the guide 119. The translation means 129 comprise an elongated flexible helical screw 131, which is actuated by actuation means 135 so as to rotate around its longitudinal axis. The external surface of the elongated flexible helical screw 131 is configured to engage with a threaded surface 611 of the guiding carriage 127, so that the rotation of the elongated flexible helical screw 131 about its own axis results in the translation of the guiding carriage 127 along the guide 119 of the articulated support, in a "screw and nut mechanism" fashion. Advantageously, since the elongated flexible helical screw 131 is flexible, the articulated support 107 is allowed to assume bent configurations, for example in its flexible rest configuration during insertion into the body cavity. The actuation means 135 comprise motor means and transmission gears 652 configured to actuate the rotation of the elongated flexible helical screw 131.

Figure 31:
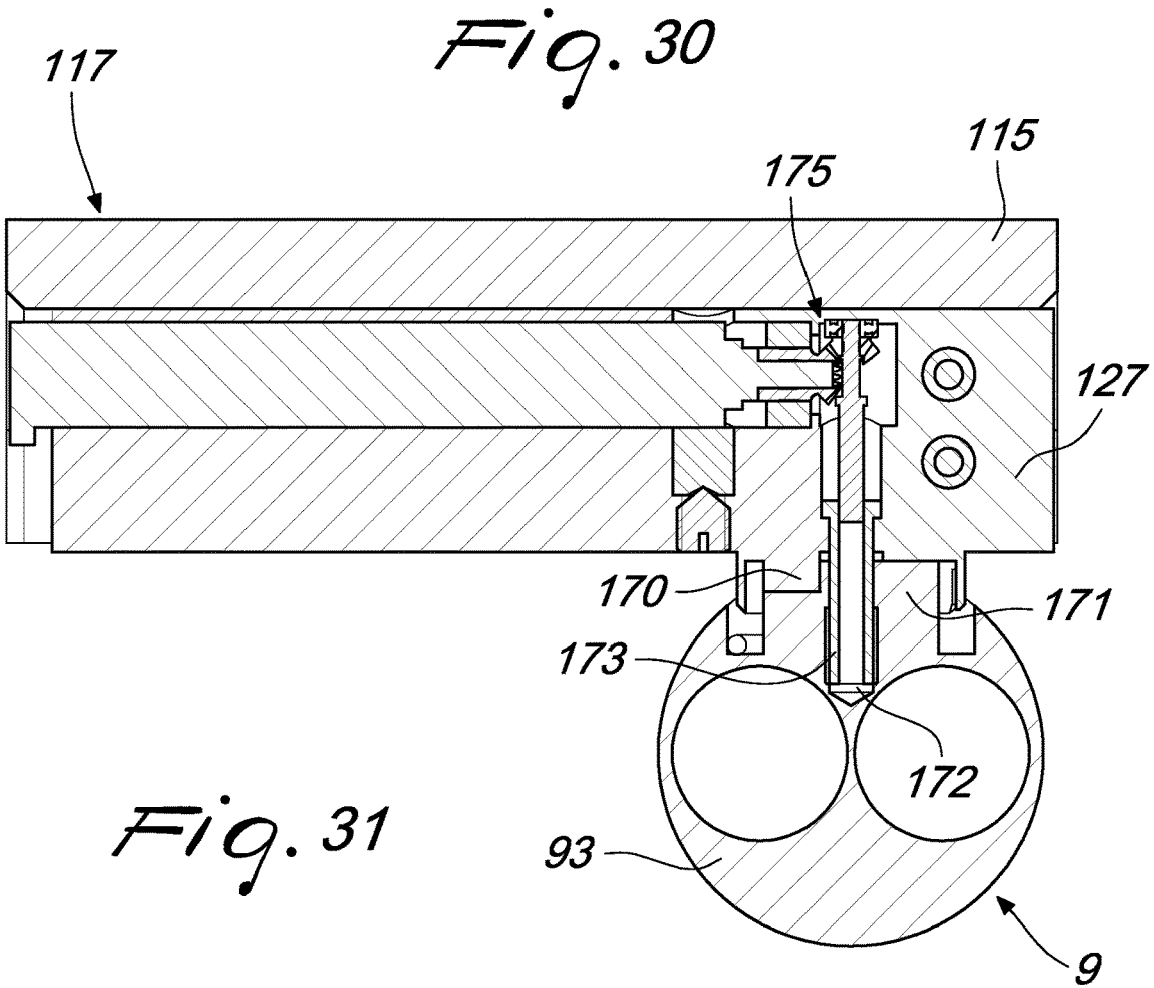
FIG. 31 is a side cross-section view of a variant of the system for fixing the maneuvering means to the articulated support shown in FIG. 24.
Figure 32:
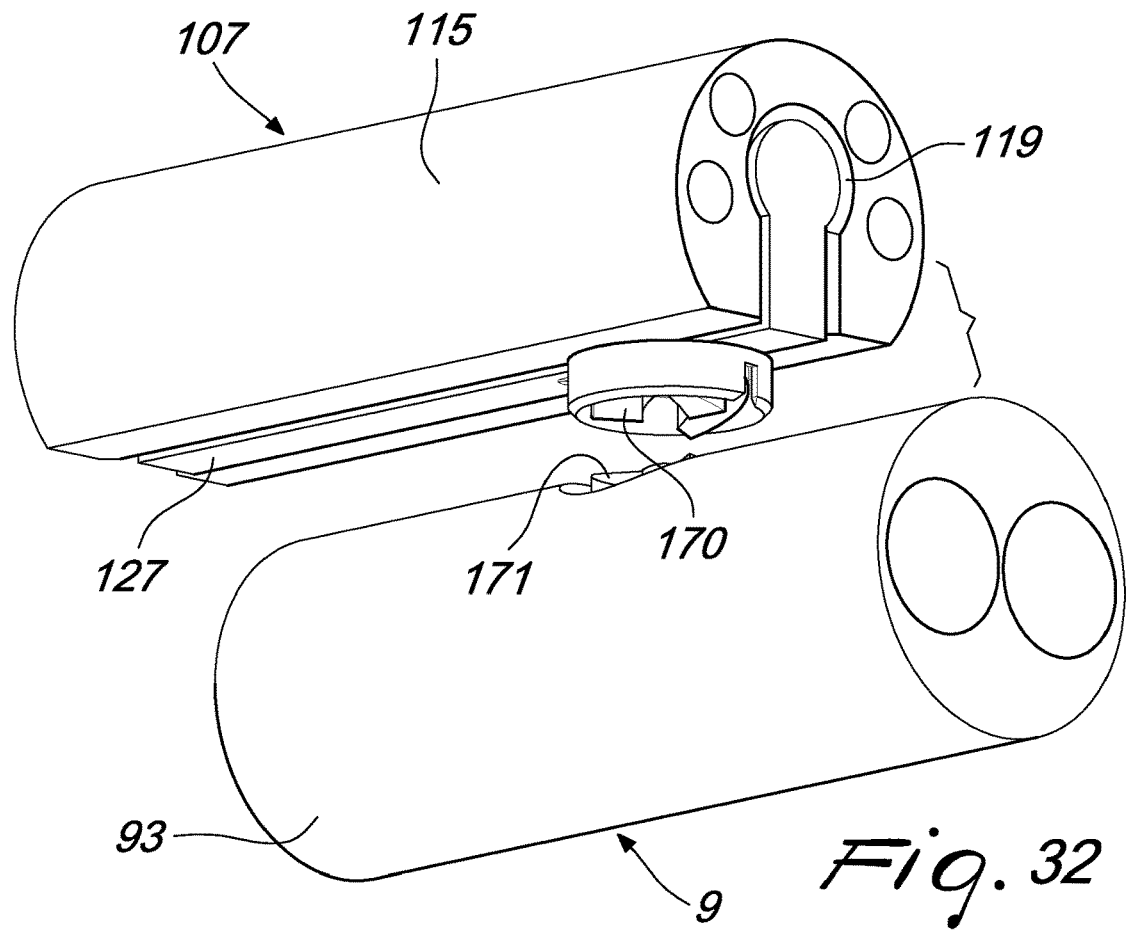
FIG. 32 is a perspective view of the fixing system shown in FIG. 31, in its pre- or post-operative configuration.
Figure 33:
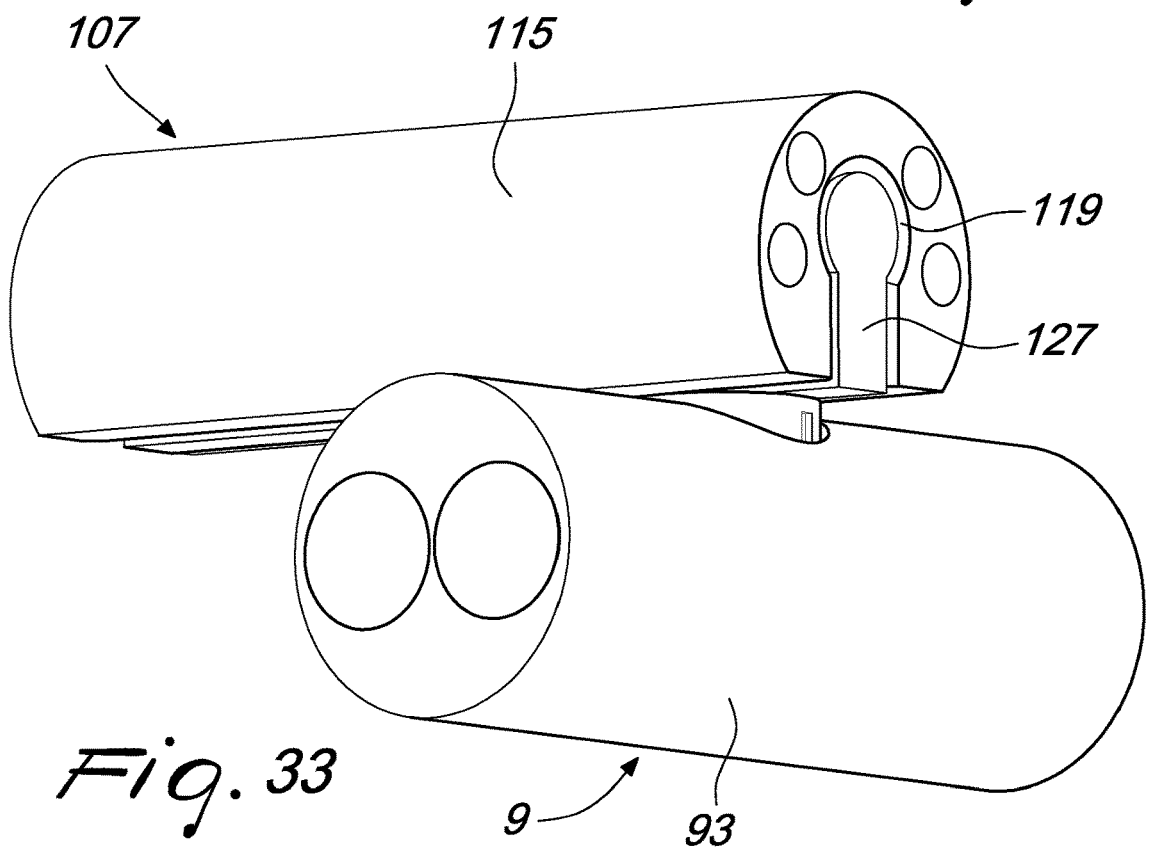
FIG. 33 is a perspective view of the fixing system shown in FIG. 31, in its operative configuration.

FIGS. 31, 32 and 33 show a variant of the blocking systems for engaging the maneuvering means 9, and particularly their supporting element 93, with the articulated support 107. The blocking system comprises an engagement screw 173 associated with the guiding carriage 127 that can slide in the guide 119 of the articulated support 107, and a threaded hole 172 provided in the supporting element 93 and adapted to accommodate the engagement screw 173. The engagement screw 173 is actuated by actuation means 175 so that, when the engagement screw 173 engages the threaded hole 172, the supporting element 93 is pulled up towards the guiding carriage 127. In addition, the guiding carriage 127 can comprise a helical element 170 adapted to engage a corresponding helical element 171 of the supporting element 93. During the vertical pulling movement, the surfaces of the helical elements 170, 171 slide one on the other, so as to force the supporting element 93 to rotate from a position parallel to the articulated support 107, to a position orthogonal to the articulated support, as shown in FIGS. 32 and 33. When the supporting element 93 is rigidly fixed to the guiding carriage 127, the angle between the supporting element 93 and the articulated support 107 is a fixed angle of about 90°.

FIG. 33 shows an operative configuration of the robot 1, in which the supporting element 93, and therefore the maneuvering means 9, are positioned at an angle of 90° with respect to the articulated support 107. In the pre- and post-operative configuration, the maneuvering means 9 can be substantially parallel with respect to the articulated support 107, as shown in FIG. 32.

The blocking system is advantageously associated with this helical coupling 170, 171, and comprises an engagement screw 173 associated with the articulated support 107 and a threaded hole 172 provided in the supporting element 93 and adapted to accommodate the engagement screw 173. The connection between the screw 173 and the hole 172 allows to fix stably and rigidly the maneuvering means 9 to the guiding carriage 127 at a fixed angle between the supporting element 93 and the articulated support 107.

Figure 28:
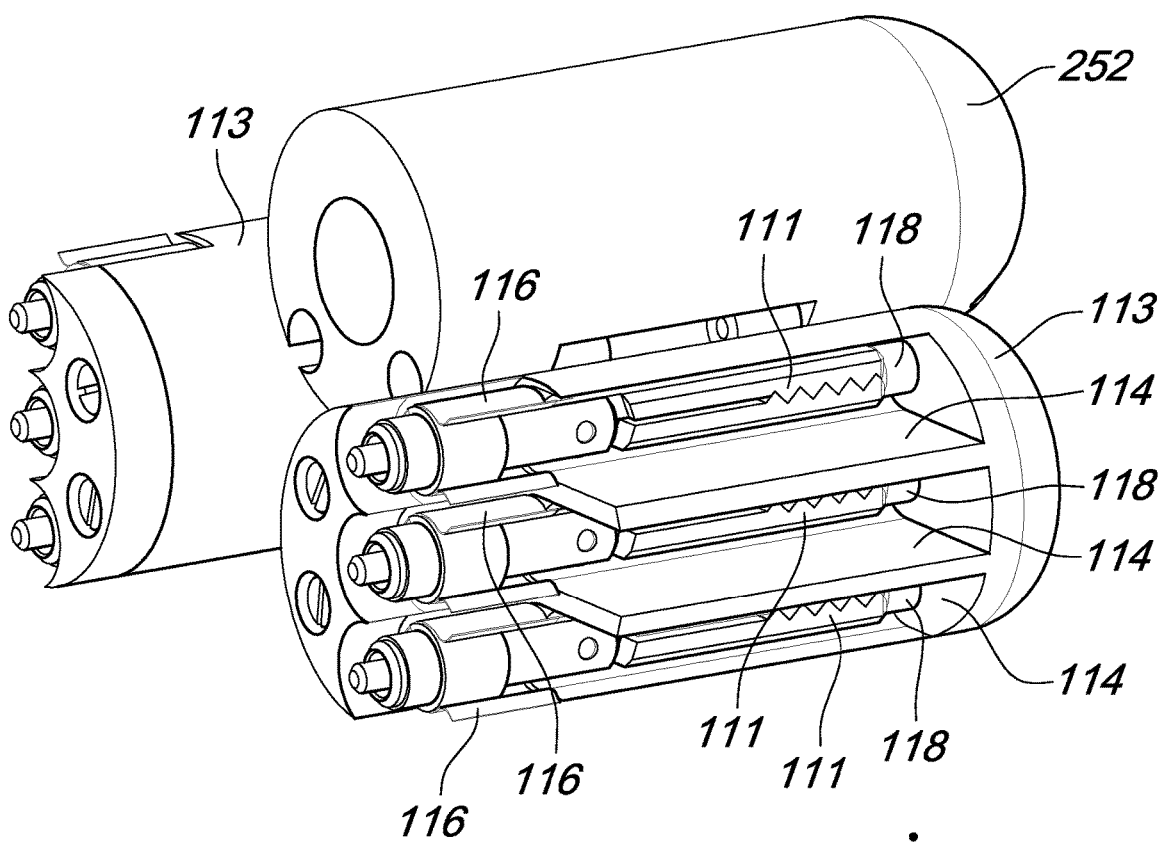
FIG. 28 is a perspective view of the portion of the articulated support shown in FIG. 24, provided with a variant of the container bodies.
Figure 29:
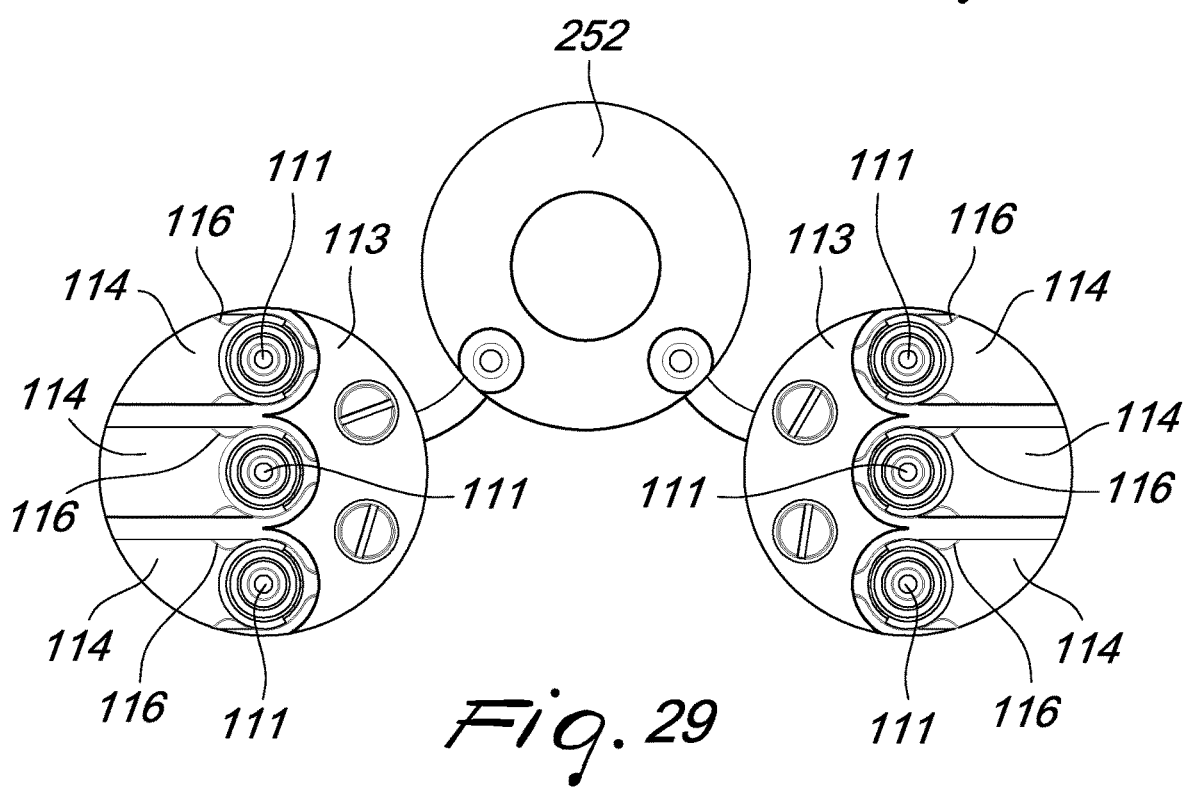
FIG. 29 is a front view of the articulated support shown in FIG. 28.
Figure 30:
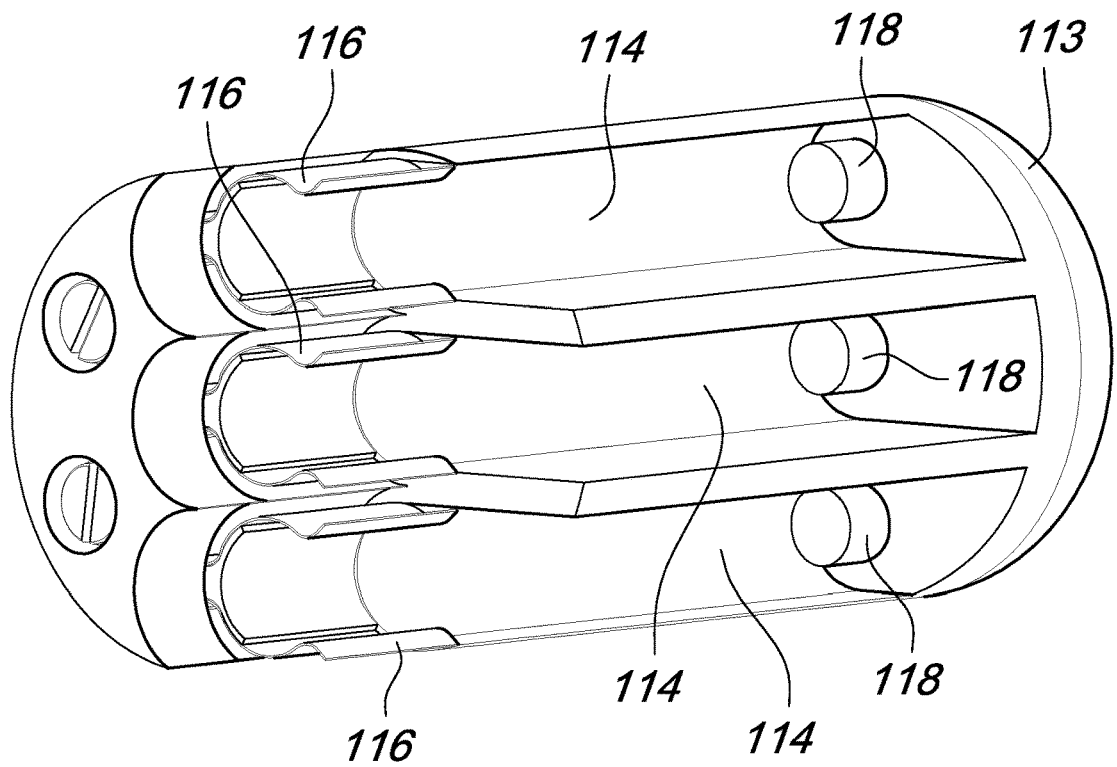
FIG. 30 is a perspective view of the variant of the container body shown in FIG. 28.

FIGS. 28, 29 and 30 show a variant of the container body 113, which is adapted to contain up to three instruments 111. The container body 113 comprises three slots 114 for accommodating the instruments 111. The slots 114 are provided with leaf springs 116, configured to stably hold the instruments 111, and with a safety sensor 118 and a retention spring adapted to check the presence, or absence, of an instrument 111 in the corresponding slot 114.

Figure 34:
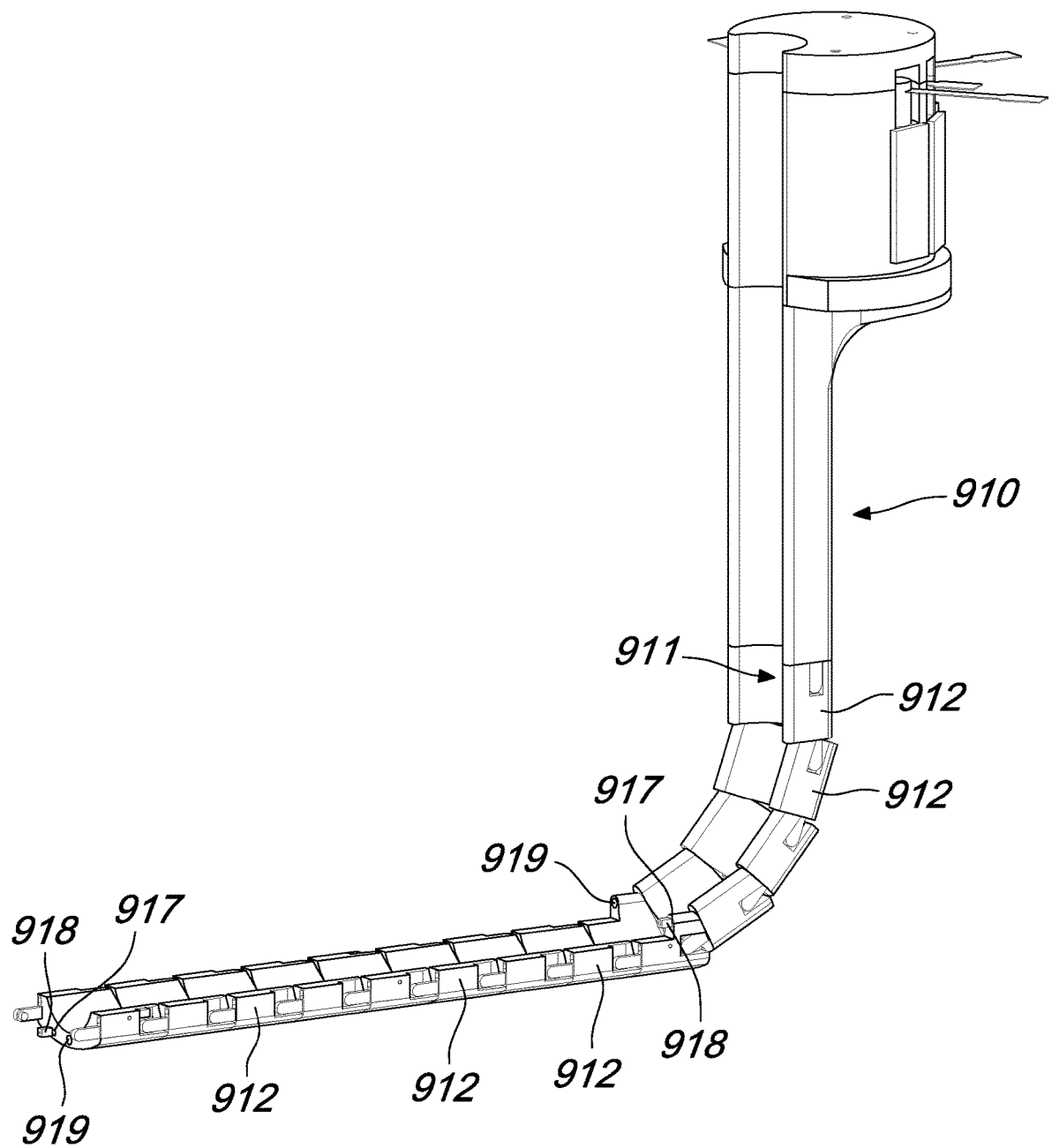
FIG. 34 is a perspective view of a variant of the insertion means.
Figure 35:
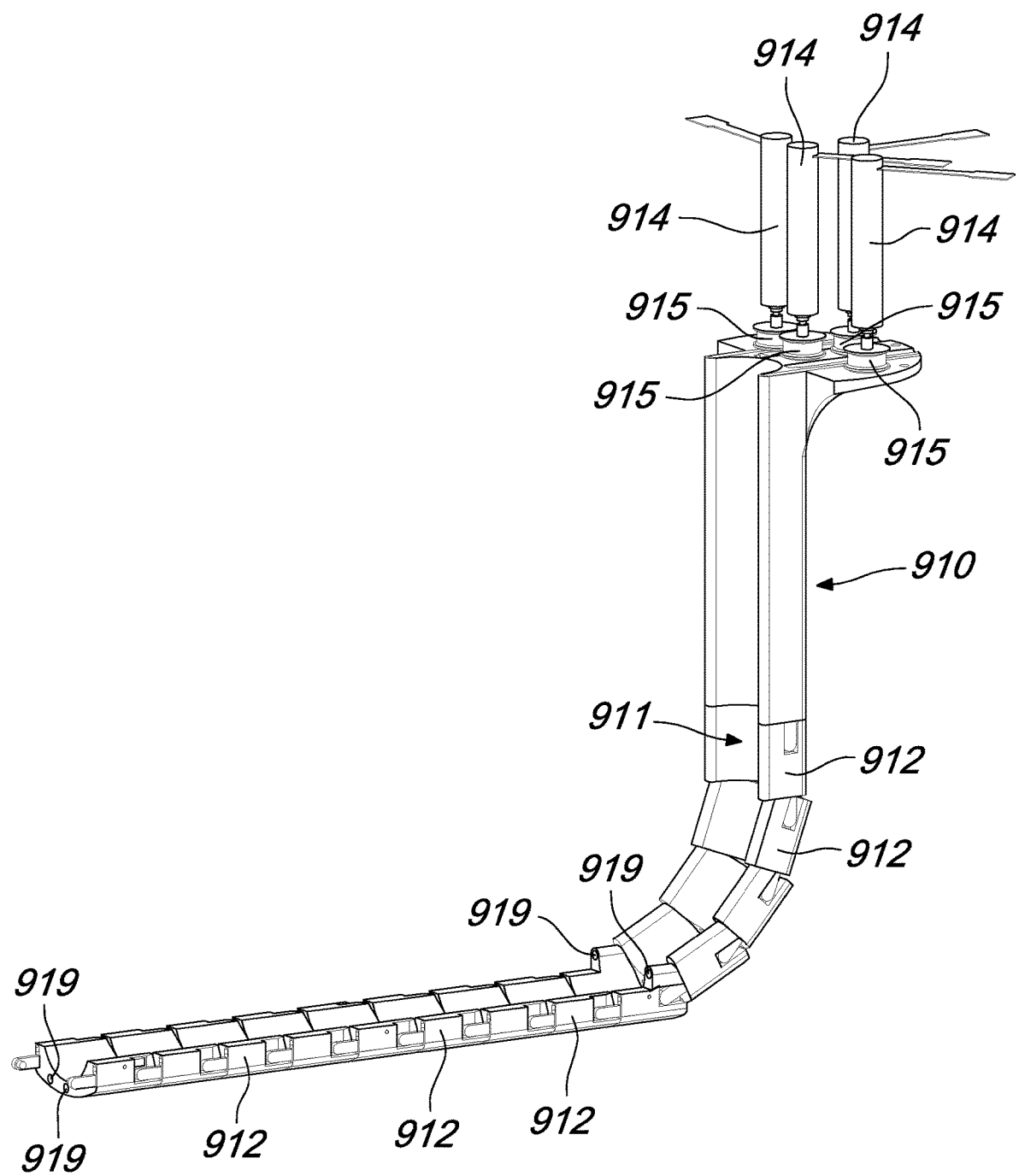
FIG. 35 is a perspective view of the insertion means shown in FIG. 34, wherein some elements have been removed.

FIGS. 34 and 35 show a variant of the insertion means 910. The insertion means 910 comprise advantageously an insertion guide 911, which is advantageously formed by a substantially tubular structure that is open on one side. This insertion guide 911 forms a substantially semicircular channel, in which the maneuvering means 9 and the articulated support 7, 107 can slide, in their flexible rest configuration. The insertion means 910 comprise a plurality of rigid elements 912, reciprocally hinged one to another so as to define the insertion guide 911. The insertion means 910 also comprise tensioning cables 917, provided with cable stoppers 918, that pass through holes 919 provided in all the rigid elements 912. Such tensioning cables are configured to rigidify the insertion guide 911, or portions thereof, when required. Advantageously, the insertion means 910 comprise motor means 914, provided with pulley 915 around which the tensioning cables 917 can wind up, in order to stiffen the whole structure, or portions thereof.

Advantageously, the insertion guide 911 can assume a substantially L-shaped configuration.

Advantageously, the above-mentioned portions of the guide 911 can bee steered independently by means of the tensioning cables 917, in order to insert the insertion guide 911 in a body cavity without touching inner body parts.

The operation of the robot is described hereinafter, with reference to an example of laparoscopic surgery through a single abdominal incision (or through a natural orifice).

First of all, the surgeon performs an incision, or prepares the natural orifice, that forms the access opening 200, through which a trocar, possibly provided with viewing means, is inserted. Then the surgical cavity is inflated.

In particular, the terminal end of the trocar 900 is shown in FIG. 23. Advantageously, said trocar 900 can have lighting means 901, such as for example LEDs, and viewing means 902, such as video cameras.

Through this trocar, the surgeon inserts the insertion means 810 in the surgical area 201.

Then the articulated support 7 is inserted in the flexible rest configuration, making it slide along the guide formed by the insertion means 810.

The correct insertion of the articulated support 7 along the guide formed by the insertion means 810 is indicated by means of calibrated reference points provided on the insertion means 810 and on said articulated support 7. Moreover, a mechanical retainer is provided which can be activated manually by the operator and blocks the insertion of the articulated support 7 along the insertion means 810 when they have reached the predefined position.

The articulated support 7 can be then connected, if it is not already, to the terminal portion 500 of the adapter 5 by means of the spherical hinge 50 and said adapter 5 is supported by the supporting structure 3, fixed to the operating table.

At this point the stiffening means 17 are activated and bring the articulated support 7 in its active rigid configuration, locking also the spherical hinge 50, which therefore becomes a rigid coupling.

The insertion guide 811 and the terminal portion 500 of the adapter 5 provide at this point a channel formed by two semicircular channels which straddle the access opening 200 of the surgical area 201.

The maneuvering means 9, constituted by the robotic arm 91 (or by a pair of robotic arms 91), provide a rest configuration, in which the articulations between the various segments are free. In this rest configuration, the maneuvering means 9 are therefore substantially flexible, in a manner similar to what occurs for the articulated support 7.

The maneuvering means 9, in their rest configuration, i.e. flexible configuration, are then inserted in the surgical area 201. They are inserted initially through the channel formed by the insertion means 810 and by the terminal portion 500 of the adapter 5, and then are made to slide along the insertion guide 811, moving beyond also the terminal end portion 814.

The insertion of the maneuvering means 9 also is assisted by the presence of calibrated reference points that are present not only on the insertion means 810 but also on said maneuvering means 9.

As shown in FIGS. 20, 21 and 22, the articulated support 7 and the maneuvering means 9, once inserted in the surgical area 201 and brought to the rigid active configuration, are in a position in which the engagement means 70, 72 of the articulated support 7 face the engagement means 71, 73 of the maneuvering means 9.

At this point the maneuvering means 9 are moved into contact with the articulated support 7 so as to engage mutually by means of the respective engaging systems.

The operation for mutual approach of the maneuvering means 9 and the articulated support 7 can be performed manually by the surgeon, who pulls toward himself the end 218 of the maneuvering means 9 that is still accessible from the outside of the access opening 200, or pulls toward himself the insertion means 810 on which the freshly inserted maneuvering means 9 rest.

As an alternative, it is possible to provide in the maneuvering means 9, or optionally in the articulated support 7, actuation and engagement means adapted to bring the respective engagement systems into mutual contact.

These actuation and engagement means can include, for example, a screw, which is driven by a motor, is arranged in the maneuvering means 9 and engages a threaded hole provided in the articulated support 7.

At this point, once the maneuvering means 9 have been fixed to the articulated support 7, the translation means 29 are actuated and move said maneuvering means 9 along the guide 19 of the articulated support 7, so that said maneuvering means 9 are inserted completely in the surgical area 201 and reach a desired position along the guide 19.

Once the maneuvering means 9 are engaged with the articulated support 7 and have reached the desired position along the guide 19, the operator can remove manually the insertion means 810. Advantageously, this removal of the insertion means 810 can occur when the maneuvering means 9 have been moved along the guide 19 in a position of noninterference with the terminal end portion 814 of the insertion guide 811.

The maneuvering means 9, which still lie substantially parallel to the articulated support 7, can now been conveniently rotated, for example through 90°, by means of the engagement systems 70, 71, 72 and 73, so that the articulated support 7 and the maneuvering means 9 assume a relative configuration such as the one shown in FIG. 1. Once they have been engaged with the articulated support 7, the maneuvering means 9 in fact are activated, passing from the rest configuration to the active configuration.

It should be noted that the container bodies 13, with the associated operating instruments 11 contained therein, have been associated beforehand with the ends of the maneuvering means 9 and therefore are inserted in the surgical area 201 together with said maneuvering means 9.

The assembly of the robot 1 also entails a step for engaging the container bodies 13 with the articulated support 7. This step entails the opening of the engagement tab 130 arranged at the end of the articulated support 7, the actuation of the maneuvering means 9 so that they move closer and engage the engagement tabs 130 in the engagement slots 131 formed in the container bodies 13, and the subsequent release of the container bodies 13 from the maneuvering means 9, once they have been stably engaged with the articulated support 7.

During this step, the viewing means 21, 21*a* are advantageously active, i.e., in the open operating configuration.

In fact, the operator can proceed with the activation of the maneuvering means 9, by moving the robotic arms 91 in order to arrange and engage with the articulated support 7 the container bodies 13, which are still engaged with the maneuvering means 9 when the surgical area 201 is viewed by the viewing means 21, 21*a*.

The maneuvering means 9 extract the required operating instruments 11 from the available container bodies 13, which are now engaged with the articulated support 7, and perform the surgical operation.

When the surgical operation is finished, any pathological tissues to be removed are extracted and removed from the surgical area and one can then proceed with the extraction of the robot 1 in reverse order with respect to the order of insertion.

Removal of the robot 1 from the surgical area 201 occurs by bringing the articulated support 7 and the maneuvering means 9 to their inactive flexible configuration. The articulated support 7 and the maneuvering means 9 can be therefore grabbed by the operator by means of a suitable forceps or similar instrument that passes through the trocar, and then extracted. As an alternative, it is possible to reinsert the insertion means 810, again by means of the trocar, in order to guide outward the articulated support 7 and the maneuvering means 9.

The procedure for changing operating instrument 11 is as follows: the forearms 97 of the robotic arm 91 are aligned with the container body 13 engaged with the articulated support 7. At this point the translational movements along the guide 19 of the maneuvering means 9 and the rotational movements of the wrist-like joint of the robotic arm 91 are used in order to move closer and engage the desired operating instrument 11. During this operation, the safety devices ensure that each operating instrument 11 is always associated with the respective container body 13, or with the maneuvering means 9, or with both at the same time.

In practice it has been found that the robot particularly for mini-invasive surgery according to the present disclosure achieves the intended aim and objects, since it allows to perform mini-invasive surgical operations in a manner that is safe for the patient without requiring a plurality of accesses to the surgical area of interest.

Another advantage of the robot according to the disclosure is that it has small dimensions and is easy to handle and therefore also fast and easy to insert and remove.

A further advantage of the robot according to the disclosure is that it can be equipped with a plurality of different operating instruments in order to perform various surgical operations.

Another advantage of the robot according to the disclosure is that it can be also used in combination with laparoscopic techniques of the standard type, since it does not occupy the surgical surface of the abdomen or of the chest with bulky devices.

A further advantage of the robot according to the disclosure is that it offers the stability and stiffness needed to transmit and apply forces and moments necessary for the surgical operation.

The robot particularly for mini-invasive surgery thus conceived is susceptible of numerous modifications and variations, all of which are within the scope of the same inventive concept.

All the details may furthermore be replaced with other technically equivalent elements.

In practice, the materials used, so long as they are compatible with the specific use, as well as the contingent shapes and dimensions, may be any according to the requirements.

The disclosures in Italian Patent Application No. MI2013A000666 from which this application claims priority are incorporated herein by reference.

Where technical features mentioned in any claim are followed by reference signs, those reference signs have been included for the sole purpose of increasing the intelligibility of the claims and accordingly such reference signs do not have any limiting effect on the interpretation of each element identified by way of example by such reference signs.

The invention claimed is:

1. A robot for mini-invasive surgery through a single parietal incision or natural orifice comprising:
at least one articulated support, which comprises a plurality of rigid bodies pivotally engaged to each other;
an imager integrated within said articulated support;
at least one tensioning element incorporated in said articulated support and configured to transition of said articulated support from an inactive configuration, in which said rigid bodies are movable relative each other, to an active configuration, in which said rigid bodies are fixed relative each other forming a guide, and vice versa;
at least one container body fixed to a distal end of said articulated support and configured to store a plurality of operating instruments simultaneously;
at least one robotic arm slidingly engaged with said guide of said articulated support in said active configuration and configured to selectively engage the plurality of operating instruments stored in said at least one container body when the articulated support is in the active configuration, while the robotic arm and the container body are disposed in a body cavity, wherein said rigid bodies have a hollow conical end and a convex conical end, wherein the hollow conical end and the convex conical end of adjacent rigid bodies are configured to engage each other by tensioning said at least one tensioning element to transition said articulated support into the active configuration;
wherein said articulated support comprises at least one guiding carriage having engagement mechanisms configured to engage with engagement mechanisms of the robotic arm enabling the robotic arm to translate and rotate with respect to said articulated support, and translation means configured to translate said at least one guiding carriage in said guide.

2. The robot according to claim 1, comprising insertion means adapted to guide said articulated support in said inactive configuration and said at least one robotic arm within a surgical area through an access opening.

3. The robot according to claim 1, wherein said container body is connected with at least one end of said articulated support.

4. The robot according to claim 1, wherein said robotic arm includes 7 degrees of freedom.

5. The robot according to claim 1, wherein said tensioning element comprises tensioning cables that pass through said articulated support and are actuated by a motor, said active configuration being obtained by shape mating of a female end with a male end of two consecutive rigid bodies.

6. The robot according to claim 1, wherein said translation means comprise at least one translation cable that is connected at one end to said at least one guiding carriage and wound, at the opposite end, on a pulley keyed to a driving shaft of a motor.

7. The robot according to claim 1, wherein said container body includes a plurality of safety devices adapted to ensure that said operating instruments are always associated alternatively with said container body or with said robotic arm.

* * * * *